(12) United States Patent
Stanke et al.

(10) Patent No.: US 6,690,473 B1
(45) Date of Patent: Feb. 10, 2004

(54) INTEGRATED SURFACE METROLOGY

(75) Inventors: Fred E. Stanke, Cupertino, CA (US);
Talat F. Hasan, Saratoga, CA (US);
Michael Weber, Sunnyvale, CA (US)

(73) Assignee: Sensys Instruments Corporation, Santa Clara, CA (US)

( * ) Notice: Subject to any disclaimer, the term of this patent is extended or adjusted under 35 U.S.C. 154(b) by 0 days.

(21) Appl. No.: 09/495,821

(22) Filed: Feb. 1, 2000

Related U.S. Application Data

(60) Provisional application No. 60/118,217, filed on Feb. 1, 1999, and provisional application No. 60/128,915, filed on Apr. 12, 1999.

(51) Int. Cl.[7] .............................................. G01B 11/24
(52) U.S. Cl. ........................ 356/601; 356/369; 356/511
(58) Field of Search ................................. 356/376, 381, 356/382, 369, 601, 602, 609, 612, 600, 485, 495, 511; 438/16, 693

(56) References Cited

U.S. PATENT DOCUMENTS

| | | | | |
|---|---|---|---|---|
| 4,659,220 A | | 4/1987 | Bronte et al. ............... 356/237 |
| 4,848,908 A | * | 7/1989 | Huang ........................ 356/489 |
| 4,869,593 A | * | 9/1989 | Biegen ....................... 356/351 |
| 5,042,949 A | * | 8/1991 | Greenberg et al. .......... 356/345 |
| 5,298,975 A | * | 3/1994 | Khoury et al. .............. 356/375 |
| 5,412,473 A | * | 5/1995 | Rosencwaig et al. ....... 356/451 |
| 5,436,725 A | | 7/1995 | Ledger ....................... 356/357 |
| 5,517,312 A | | 5/1996 | Finarov ...................... 356/386 |
| 5,604,344 A | | 2/1997 | Finarov .................... 250/201.3 |
| 5,616,063 A | * | 4/1997 | Okumura et al. ............. 451/1 |
| 5,695,601 A | * | 12/1997 | Kodera et al. ........... 156/636.1 |
| 5,747,813 A | | 5/1998 | Norton et al. ............. 250/372 |
| 5,757,502 A | * | 5/1998 | Weling ....................... 356/376 |
| 5,764,365 A | | 6/1998 | Finarov ...................... 356/381 |
| 5,825,498 A | | 10/1998 | Thakur et al. ............. 356/394 |
| 5,835,225 A | * | 11/1998 | Thakur ....................... 356/381 |
| 5,948,203 A | * | 9/1999 | Wang ......................... 156/345 |
| 6,108,091 A | * | 8/2000 | Pecen et al. ................ 356/381 |
| 6,108,092 A | * | 8/2000 | Sandhu ....................... 356/382 |
| 6,142,855 A | * | 11/2000 | Nyui et al. ................... 451/67 |
| 6,157,450 A | * | 12/2000 | Marchese-Ragona et al. .... 356/376 |

FOREIGN PATENT DOCUMENTS

| | | | | |
|---|---|---|---|---|
| EP | 0 881 484 A2 | 12/1998 | .......... G01N/21/00 |
| GB | 2 314 037 A | 12/1997 | ............ B23Q/1/36 |
| WO | WO 98/37404 | 8/1998 | .......... G01N/21/00 |
| WO | WO 99/01797 | 1/1999 | ............. G03F/7/20 |

OTHER PUBLICATIONS

L. Li, "Multilayer modal method for diffraction gratings of arbitrary profile, depth, and permittivity," *Jour. Opt. Soc. of Am. A*, vol. 10, No. 12, 1993, pp. 2581–2591.

P.S. Hauge, "Polycrystalline silicon film thickness measurement from analysis of visible reflectance spectra," *J. Opt. Soc. Am.*, vol. 69, No. 8, Aug. 1979, pp. 1143–1152.

H. Engstrom, "Measuring thickness of a film deposited onto a multilayer metal surface," *SPIE vol. 1673 Integrated Circuit Metrology, Inspection, and Process Control VI*, 1992, pp. 432–440.

(List continued on next page.)

*Primary Examiner*—Hoa Q. Pham
(74) *Attorney, Agent, or Firm*—Stallman & Pollock LLP

(57) ABSTRACT

This invention is an instrument adaptable for integration into a process tool the combines a number of instruments for surface characterization. As an integrated process monitor, the invention is capable of monitoring surface dishing, surface erosion and thickness of residue layers on work-pieces with little time delay. The invention is adaptable to making measurements while a wafer or work-piece is either wet or dry. A preferred embodiment includes an integrated optical profiler adapted to surface profiling in the presence of optical interference arising from retro-reflections from underlying optical non-uniformities. Alternate embodiments include an integrated stylus profiler with vibration isolation.

9 Claims, 35 Drawing Sheets

OTHER PUBLICATIONS

G.E. Jellison, Jr., "Data analysis for spectroscopic ellipsometry," *Thin Solid Films*, vol. 234, 1993, pp. 416–422.

*The Handbook of Optics, vol. II*, by Rasheed M.A. Azzam, "Chapter 27—Ellipsometry," and "Chapter 28—Spectroscopic Measurements," Michael Bass, ed., McGraw Hill, Inc., New York, 1995, pp. 27.1–28.6.

T.R. Corle et al., "Differential interference contrast imaging on a real time confocal scanning optical microscope," *Applied Optics*, vol. 29, No. 26, Sep. 10, 1990, pp. 3769–3774.

C.J. Morath et al., "Ultrasonic multilayer metal film metrology," *Solid State Technology*, Jun. 1997, pp. 85–92.

D. Boning et al., "MIT/SEMATECH 931AZ Copper (Cu) Chemical/Mechanical Planarization Test Chip Design, Layout, and Electrical Test," *SEMATECH Technology Transfer #98103580A–TR*, 1998, 56 pages in length.

C.M. Peyne et al., "Test Structures for Characterising a Damascene CMP Interconnect Process," *Proc. IEEE 1997 Int. Conference on Microelectronic Test Structures*, vol. 10, Mar. 1997, pp. 151–155.

M.A. Joffe et al., "Novel Thin–Film Metrology for CMP Applications," *1999 Proceedings of the Fourth International Chemica–Mechanical Planarization for ULSI Multilevel Interconnection Conference (CMP–MIC)*, 1999, pp. 73–76.

G. Hong et al., "Three–dimensional optical profiler using Nomarski interferometry," *SPIE Proceedings*, vol. 1994, Fabrication and Testing of Opticas and Large Optics, 1994, Meeting Date Jul. 11–Jul. 16, 1993, San Diego, CA, USA, pp. 150–153.

D.L. Lessor et al., "Quantitative surface topography determination by Nomarski reflection microscopy. I. Theory," *J. Opt. Soc. Am.*, vol. 69, No. 2, Feb. 2, 1979, pp. 357–366.

J.S. Hartman et al., "Quantitative surface topography determination by Nomarski reflection microscopy. 2: Microscope modification, calibration, and planar sample experiments," *Applied Optics*, vol. 19, No. 17, Sep. 1, 1980, pp. 2998–3009.

X. Niu et al., "Specular Spectroscopic Scatterometry in DUV Lithography," *SPIE 24th International Symposium on Microlithography*, SPIE Paper 3677–18, 1999, 10 pages in length.

S.A. Coulombe et al., "Ellipsometric–Scatterometry for sub–0.1 $\mu$m CD measurements," *SPIE*, vol. 3332, 1998, pp. 282–293.

J. Bischoff et al., "Optical scatterometry of quarter micron patterns using neural regression," *SPIE*, vol. 3332, 1998, pp. 526–537.

T. Ganz et al., "Microellipsometry," see http://gastno.iap-.physik.tu–darmstadt.de/omt/jb97_mic.ps, 1977 Annual Report, 3 pages in length.

H. Jennewein et al., "Interferometrical Profilometry at Surfaces with Varying Materials," *SPIE 24th International Symposium on Microlithography*, SPIE Paper 3677–109, 1999, 9 pages in length.

G. Springer, "Dependence of wafer carrier motor current and polish pad surface temperature signal on CMP consumable conditions and Ti/TiN linear deposition parameters for Tungsten CMP endpoint detection," *1999 Proceedings of the Fourth International Chemical–Mechanical Planarization for ULSI Multilevel Interconnection Conference (CMP–MIC)*, 1999, pp. 45–51.

\* cited by examiner

INTEGRATED SURFACE METROLOGY

CROSS-REFERENCE TO RELATED PROVISIONAL APPLICATION

This application claims the benefit of U.S. Provisional Application, Serial No. 60/118,217, filed Feb. 1, 1999, and U.S. Provisional Application Serial No. 60/128,915, filed Apr. 12, 1999, both of which are hereby incorporated by reference.

BACKGROUND

1. Field of the Invention

This invention relates to methods and apparatus for surface metrology in general, and more particularly to methods and apparatus for integrated surface metrology.

2. Description of the Related Art

In order to achieve smaller device sizes, the microelectronics industry is moving towards the use of a dual Damascene process with typically more than five layers of copper interconnects. To implement a dual Damascene process, Chemical Mechanical Polishing (CMP) of copper in an environment with mixed copper and dielectric circuit underlying structures is a critical technology.

In the overall process flow for integrated circuit manufacturing, arrays of alternating lines of copper and spaces of oxide are built-up on wafers in order to construct electrical circuits. In the building-up process, both copper circuit lines and the oxide spaces that separate copper circuit lines are covered with copper just prior to a CMP step. That is, the entire wafer surface is covered with copper with oxide structures buried beneath a covering layer. The CMP process step then removes the copper above the oxide spaces without over-polishing or under-polishing. In the art, over-polishing refers to stopping the polishing process after the copper over the oxide spaces has been cleared and under-polishing refers stopping the polishing process before the copper over the oxide is cleared. In practice, slight over-polishing may be necessary to prevent device failures caused by excess copper acting to bridge lines and spaces. Such bridging provides a current path between adjacent lines and causes electrical short circuits.

While slight over-polishing may be necessary to avoid short circuits, even slight over-polishing introduces significant problems to the realization of the technology. During over-polish, both copper metal and dielectric are exposed and polished. Since copper polishes at much greater rate than dielectric material, a wafer's surface may tend to be non-planar at the conclusion of a CMP processing step. Further, excessive over-polishing may also give rise to excessive dishing and erosion of the wafer surface. Dishing is the difference in the level between the top surface of a copper line and the top surface of the neighboring oxide. Erosion refers to the level of oxide spaces compared to neighboring 'field oxide' that is not broken up by copper lines. Non-planarity introduced by dishing, erosion or otherwise, causes further problems that degrade device performance and make subsequent process steps more difficult. For example, structures do not have the proper electrical resistance or capacitance when non-planar. Also, optical depth of focus for a subsequent photo-lithography step is adversely affected, especially as device sizes shrink [4]. Further, the non-planar structure may cause a following CMP step to produce unwanted 'puddles' of copper in the depressions that can cause electrical short circuits.

Proper realization of copper CMP, then, carefully optimizes the amount of polishing to balance the conflicting goals of avoiding residual copper due to under-polishing and avoiding dishing and erosion due to over-polishing. The problem of realizing the technology is further complicated by the fact that the polishing rate is variable across the wafer; variable from wafer-to-wafer and wafer lot-to-wafer lot. Properties of polishing slurries, polishing pads, and wafer patterns also vary. Thus, in practical application, the correct amount of polishing to apply to a wafer is not known, a priori. What is needed is integrated metrology measurements of relevant parameters to enable adequate control the CMP process during polishing.

Prior art devices for wafer metrology fall into three general catagories: integrated thin-film thickness metrology systems (ITMs); stylus profilometers, including mechanical profilers and atomic force microscopes (AFM); and combined interferometers/optical microscopes. As described below, prior art devices are inadequate for the problem at hand.

Prior art integrated thin-film thickness metrology systems (ITMs) are typified by those manufactured by: Nova® Instruments (Israel); Nanometrics U.S.); and Dainippon Screen Mfg. Co., (Japan). ITM machines measure the thickness of transparent films at predetermined sites by optical methods. The devices typically include: a reflectance spectrometer; an algorithm for 'inverting' measured reflectance to infer film thickness; a robotic system for vision and motion control; and a training procedure for instructing the instrument where to measure the thickness. Prior art ITMs specifically address the needs for inspection of dielectric CMP by measuring the starting pre-CMP and post-CMP thickness of transparent dielectric layers, such as $SiO_2$ ('oxide'). The Nova® instrument is capable of measuring the wafers while they are wet. The remaining above-identified prior art instruments operate under dry wafer conditions. It is noteworthy that each and every of the above-identified prior art devices measure the thicknesses of locally uniform thin films. None measures profiles across a wafer.

Stylus profilometry, either with mechanical profilers or atomic force microscopes (AFM), measures profiles across wafers. In this type, the KLA-Tencor HRP machine has become an industry standard due to its high precision and long scan capabilities. Typical scans with the HRP take 10 seconds or more, for a single line scan. In general, profilers of this type are sensitive to vibration, and are typically mounted on dedicated vibration-damping supports. The instruments are typically used for test and development purposes, not on the manufacturing floor. Moreover, these instruments are implemented as standalone metrology tools, not suitable for integration into a CMP machine.

Numerous microscopic optical profiling methods utilize interferometry. Most are suitable for profiling optically homogeneous and simple surfaces. A homogeneous, rough surface is one whose optical properties from point-to-point are substantially invariant, but whose surface height relative to a reference varies with position. An example is a rough surface of a homogeneous volume of a material like either silicon dioxide ('oxide') or copper. The term-of-art, "profiling," here refers to measuring the relative heights of two or more points on the rough surface. A simple surface is one whose reflectivity depends only on the optical properties of the ambient medium and the optical properties of the object at the surface.

Some prior art optical profilers are suitable for optically heterogeneous surfaces. Jennewein et al. [20] measured profiles on simple, heterogeneous, rough surfaces (for example, gold lines on a glass substrate) with optical profiling. The absorption properties and thickness of the gold was such that light does not penetrate through the gold and back to the top surface after reflection at a gold-glass interface. Thus, the reflectivity of the gold surface in contact with the air depended only on the optical properties of the gold at that surface, and not on the thickness of the gold or on the optical properties or thickness of the glass substrate. The substrate, in turn, was presumed to be thicker than the correlation length of the optical interferometer so that was effectively infinite in extent. As a result, the reflectivity of the substrate was dependent on the optical properties of the glass at its surface. Jennewein combined measurements from an ellipsometer to measure the optical properties of the surface with phase profiles from a common-path interferometer to yield an optical profile of the surface that closely matched a mechanical profile of the same surface.

As can readily be appreciated by one skilled in the art, the prior art in optical profilometry does not address the case of relevance in copper CMP-related applications. In the prior art, the incident light did not penetrate the surface sufficiently to interact with another structure. In copper CMP applications, the polished surface and underlying oxide structures will result in profiling in the presence of optical interference arising from retro-reflections from underlying copper-oxide interfaces. Here the prior art is inadequate.

What is needed, then, is a metal CMP integrated process monitor capable of monitoring dishing, erosion and thickness of residue layers on work-pieces with little time delay. An optical device must be adapted to profiling in the presence of optical interference arising from retro-reflections from underlying interfaces and diffraction from grating-like structures. Such an invention should be adaptable to making measurements while a wafer or work-piece is either wet or dry.

SUMMARY OF THE INVENTION

An object of this invention is to provide a metal CMP integrated process monitor capable of monitoring dishing, erosion and thickness of residue layers on work-pieces with little time delay and adaptable to making measurements while a wafer or work-piece is either wet or dry. An optical device adapted to profiling in the presence of optical interference arising from retro-reflections from underlying interfaces is also provided. The invention provides a profiler to the CMP tool not in mere combination, but in full integration measuring the profile of the top surface of a wafer either before or after it has been polished, or between polishing steps. Further, the invention can detect the presence of residual copper in undesirable locations. A first embodiment uses thin-film thickness characterization and locates residue in precisely determine locals. A second embodiment uses image pattern recognition and searches large areas for residues. Further embodiments measure field thinning and thin-film stacks.

A second object of this invention is to measure profiles over optically heterogeneous structures and particularly the top layers of layered stacks. Embodiments of the invention include combinations of a phase profiler and a reflectometer and may be further integrated with a polishing machine. Alternate embodiments of the invention are as a standalone metrology tool.

A third object of this invention to provide a quantitative differential interference microscope (QDIC) to profile grating stacks. According to the invention, two QDIC phase slope profiles with the positions of the orthogonal polarizations interchanged are measured.

A further object of this invention is to provide suitable test structures for measuring topography over layered stacks.

In a preferred embodiment, the integrated surface measurement system (ISMS) apparatus includes a QDIC; an imaging normal incidence reflectometer (NIR); a microscopic imaging system; and a positioning system including stages, motors and pattern recognition capabilities. According to a preferred method, when the wafer is presented to the ISMS, the ISMS moves to predetermined locations to measure the profile, and to other locations to look for undesirable residual copper, and to other locations to measure the thickness of oxide after polishing. The ISMS reports the results of measurements: dishing, erosion, presence of residuals, and layer thickness to a control system that adjusts polishing machine control parameters for subsequent wafers and for subsequent polishing of the current wafer

DETAILED DESCRIPTION

Throughout this specification several abbreviated descriptions are routinely used as terms of art. They are not meant to be limiting. "Copper" refers to the top material that is polished in a damascene process. In a preferred embodiment, this is actually the element copper and some barrier material, eg, tantalum or tantalum nitride. "Oxide" refers to the lower material in the damascene process. This is typically silicon dioxide though it also includes by "low-k" dielectrics. "Damascene" includes "dual damascene". The complex optical index, the index and absorbtivity (n&k), and the optical properties are synonymous.

The ISMS is an instrument adaptable for integration into a process tool combining a number of instruments for surface characterization. In its most basic form, it is an integrated profiler. A preferred type of profiler is an optical profiler, it being preferable because of speed, not touching the sample, and (in some embodiments) insensitivity to vibration. However, alternate embodiments comprise an integrated stylus profiler with vibration isolation.

Figure 34:
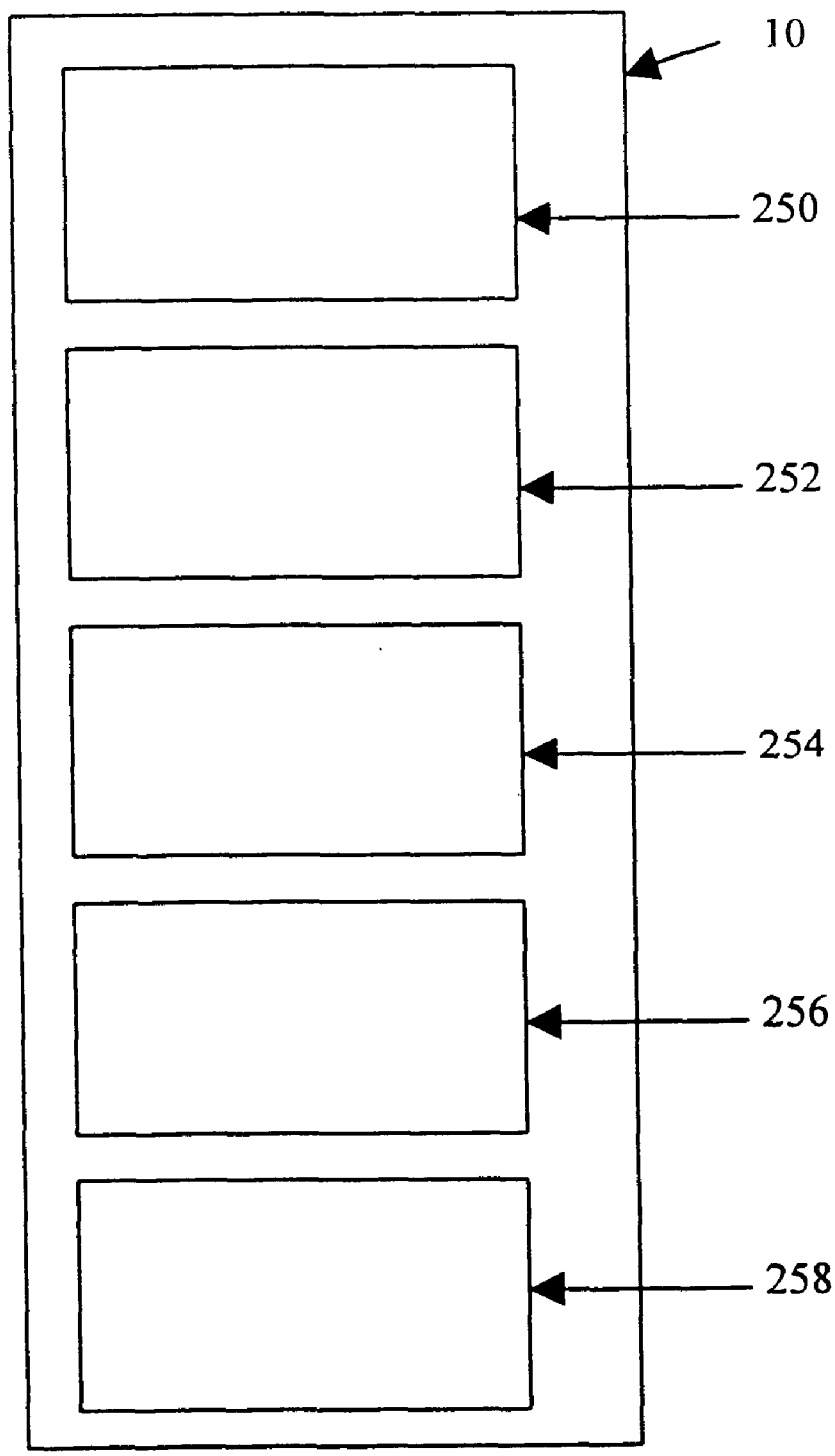
FIG. 34 schematically shows the major components in the preferred ISMS.
Figure 35:
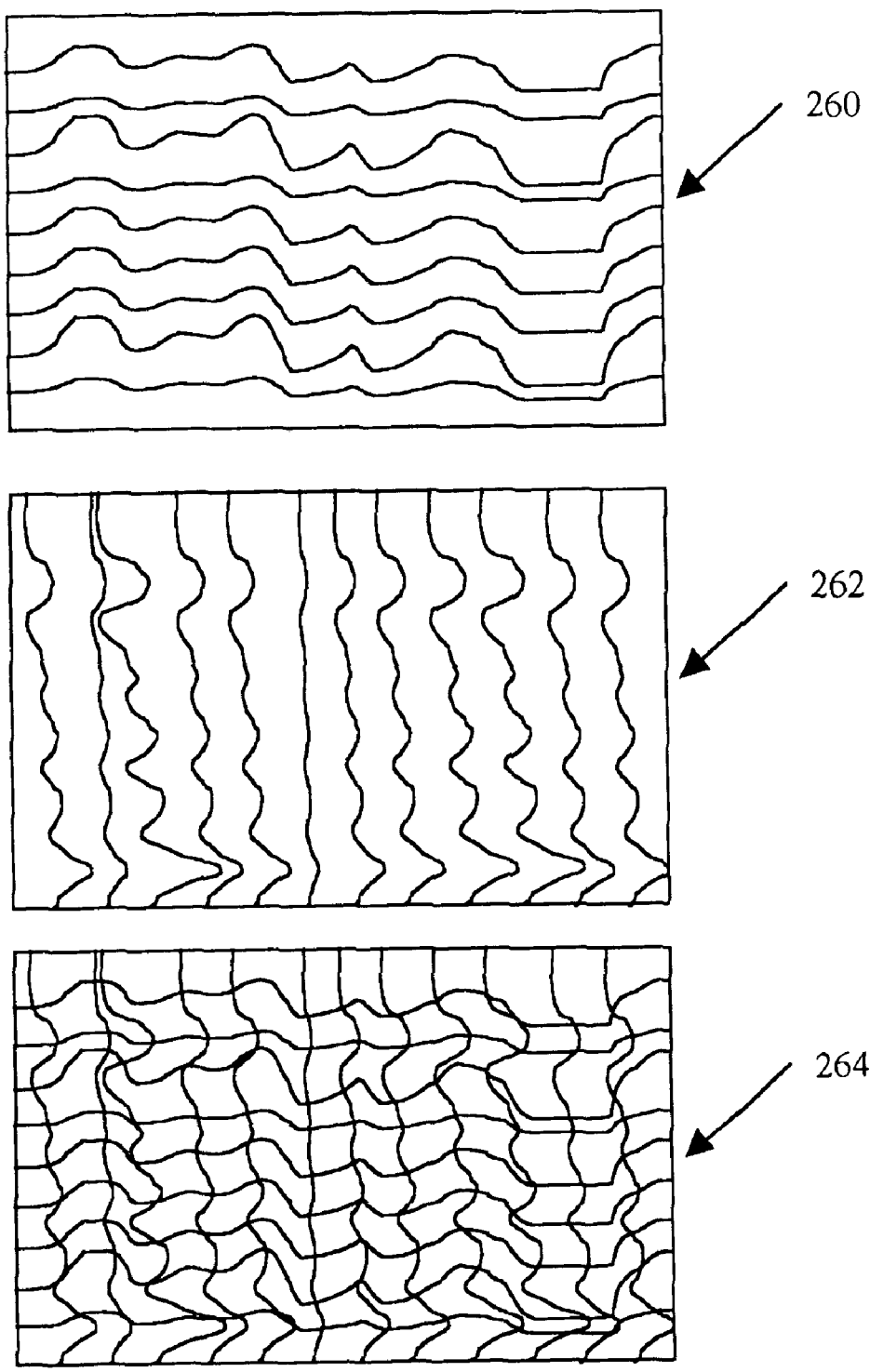
FIG. 35 illustrates a method for measuring a two-dimensional profile with the ISMS from two sets of one-dimensional profiles.

FIG. 34 schematically shows the major components in a preferred embodiment of the ISMS. FIG. 34 schematically shows the major components: interferometer 250, characterization 252, imaging system 254, positioning system 256, and wafer orienter 258.

Interferometer 10 measures the relative optical phase at predetermined points on the wafer. This may be a scanning profiler, but is preferably an imaging profiler. It is preferably a common-path interferometer, but it need not be. Common types of profilers include: differential interference contrast, quantitative differential interference contrast, and other types of polarization-based, common-path interferometers, Mirau, Michelson, white-light, point-diffraction interferometry, phase-shift interferometry, and heterodyne interferometry, phase retrieval from transport-of-intensity. Many of these techniques can be enhanced by confocal illumination techniques.

Characterization instrument 252 measures the parameters of stacks of material on the wafer. The stacks may be simple stacks, uniform stacks or grating stacks, as discussed below. The parameters may be thicknesses, optical-constant parameters, or grating-geometry patterns. This instrument may be a reflectometer, or and ellipsometer, or a scatterometer. The ellipsometer may be simple or spectroscopic or multi-angle. The characterization instrument may be an imaging instrument, or a single-point instrument.

Imaging system 254 determines precise locations on the wafer with respect to patterns on the wafer. The imaging system include the optical hardware for making images, and pattern recognition software for using the images to determine the positions of predetermined locations and directions to be measured, and a facility to train the predetermined positions and directions. The optical hardware of the imaging system may be shared with the interferometer 250 and characterization instrument 252. In some cases one of those instruments will serve the function of the imaging systems hardware component. In many cases the imaging system will have multiple fields of view, as in a microscope with a turret and objectives with different magnifications.

Positioning system 256 controls the relative position of the wafer and the optics, to allow the optics to make measurements at predetermined locations and directions on the wafer. For integrated applications, positioning system 256 preferably primarily moves the sensing portion of the instrument, to maintain a footprint that is less than twice the wafer dimension in any direction. The positioning system may use any coordinate systems for postioning, eg, Cartesian or polar coordinates.

Wafer orienter 258 may be a subset of the imaging system or a separate system consisting of hardware and software. Many types of wafer orienters are known in the art.

While the preferred embodiment of ISMS 10 includes all the components in FIG. 34x, all embodiments do not include all the components. Depending on the application, any of the components may be excluded. Also, there are other components that may be included in the ISMS. Examples are a bar-code reader or other means of identifying the wafer that is in ISMS 10, and a system to keep the wafer wet.

Figure 1:
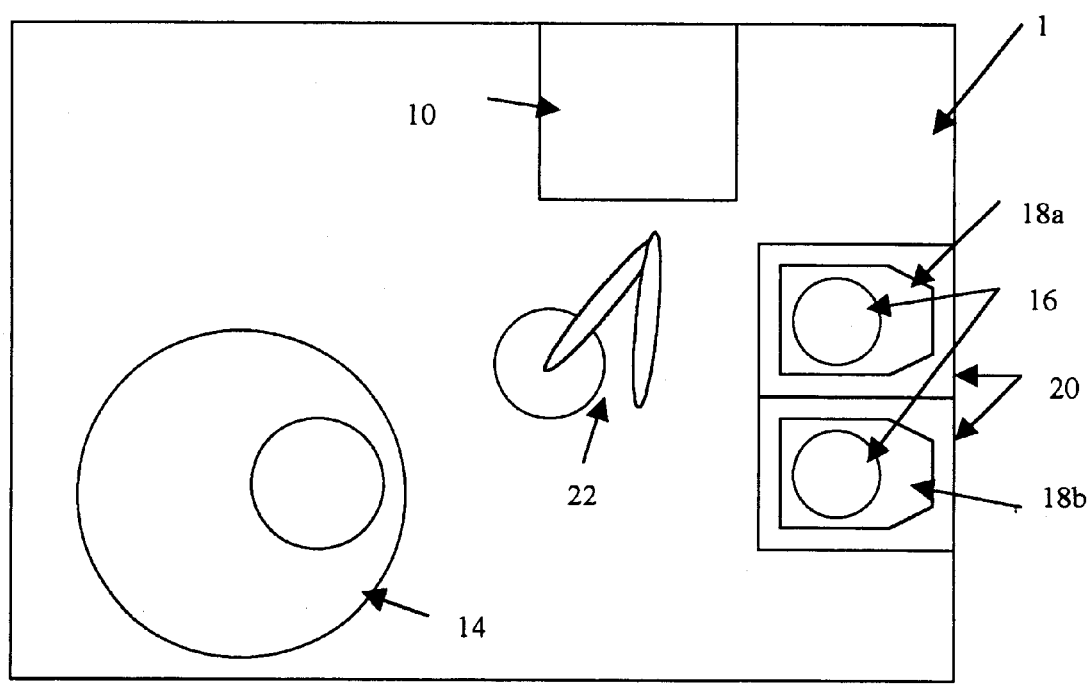
FIG. 1 is the top view of a dry-in/wet-out polishing machine with a wet ISMS integrated in the machine.

FIG. 1 shows another preferred embodiment of the invention. A polishing machine 1 and an integrated surface metrology system, ISMS 10, are shown. The polishing machine 1 comprises a polishing unit 14, loading areas 18 and transport system 22. In addition wafers 16 in carriers 18 are shown.

Wafers 16 are brought to and taken from polishing machine 1 in carriers 18 through loading areas 20. The carriers may be cassettes or FOUPs, terms common in the art. Transport system 22 is a device or set of devices for transporting the wafers within polisher 1. Specific embodiments may comprise a robot, such as the EquipeWTM-105. The transport system can move the wafers to any of the carriers 18, the polishing unit 14 or the ISMS 10.

Numerous embodiments of the invention are immediately apparent. Polishing unit 14 may take many forms, as recognized by one skilled in the art. Also, the polishing machine may comprise multiple polishing units that may be used in parallel to increase machine throughput or in series with different polishing parameters to improve the quality of polish. Exemplary embodiments include polishing machines with various types and numbers of polishing units such as those by Applied Materials, PEC/Speedfam, Ebara, Lam, Strassbaugh, and other vendors. In specific embodiments, there may be more than two loading areas 20, to accommodate higher wafer throughput. Other embodiments may include a plurality of ISMS. In a particular embodiment, one ISMS is dedicated to pre-polishing measurement of dry wafers and the other ISMS to post-polishing measurement of wet wafers. Further, transport system 22 may include holding stations or wafer buffers to facilitate transportation. Additional embodiments may also include stations along the wafer's path, eg, a rinse station after the polishing unit that removes the bulk of slurry particles from the wafer. In most embodiments, the polishing machine has mechanisms for keeping wafers wet as they are transported within the polishing machine, such as a squirter device. Capabilities and advantages of different embodiments are discussed below in detail.

In one embodiment of the method of operation of the above-described apparatus, a full carrier 18b of dual damascene wafers 16 with electro-deposited copper is loaded into the loading area 20. The transport system sequentially moves wafers from carrier 18b to polishing unit 14 for planarization, to ISMS 10 for post-measurement, and to carrier 18a for removal from polishing machine 1. In this particular embodiment, wafers are wet for the post-measurement. In the post-measurement, ISMS 10 measures dishing and erosion, and detects the presence of residual metal or barrier on the wafer as functions of position on the wafer. According to the preferred method, information from this post-measurement is subsequently used to evaluate the quality of planarization and to optimize the process for subsequent wafers; in particular regarding the amount of over-polish.

Numerous alternative embodiments of the above-described method are immediately apparent. Wafers may return to the same cassette that they arrived in. Wafers may be returned to the polishing unit after post-measurement for rework. Wafers may return to the ISMS after rework. Wafers may go to ISMS for pre-measurement before going to the polishing unit. In a particular embodiment, the pre-measurement on the ISMS measures the thickness and uniformity of the opaque layer to be polished. Information from the pre-measurement is used to control the polishing parameters of the polishing unit for the pre-measured wafer, eg, polishing time, velocities and forces. In other embodiments, the layer to be polished is damascene tungsten or aluminum or another metal or another alloy.

Figure 2:
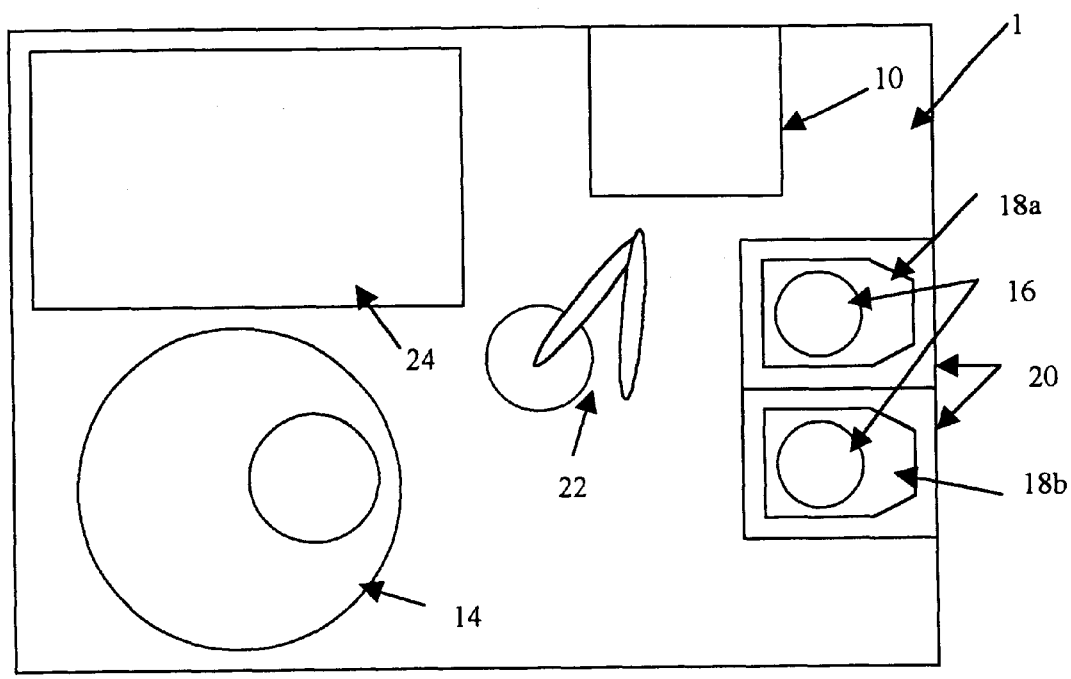
FIG. 2 is the top view of a dry-in/dry-out polishing machine with a dry ISMS integrated in the machine.

An alternative embodiment of the apparatus of the invention is shown in FIG. 2. In FIG. 2, the polishing machine comprises cleaner/dryer 24 in addition to the elements described in FIG. 1. In another embodiment of the method associated with apparatus of FIG. 2, transport system 22 transfers the wafers from polishing unit 14 to the cleaner/dryer and then to the ISMS. In this embodiment, the ISMS measures the wafers after they have been polished, cleaned and dried, and has no need to accommodate wet wafers.

In a further embodiment of the method associated with the apparatus of FIG. 2, the transport system transfers the wafer to the ISMS directly from the polishing unit while the wafer is still wet. After the ISMS measures the wafer, transport system 22 takes the wafer to the cleaner/dryer for cleaning and drying, and then to cassette 18b. This embodiment has the advantage over the previously described method in that there is less delay between when a wafer is polished and when it is measured. This reduces a feed-forward delay for the control system, and gives a more stable overall process. The disadvantage of this relative to other embodiments is that the ISMS must measure the wafers while they are wet, which leads to a degradation of capability and increased complexity, as set forth below.

Figure 3:
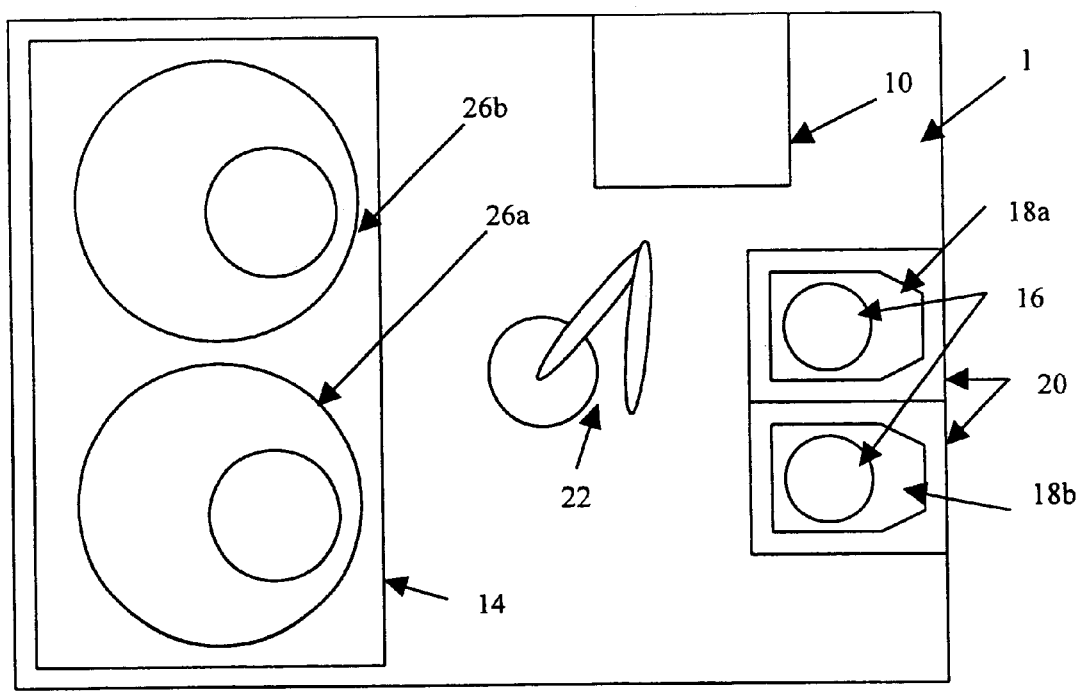
FIG. 3 is the top view of a polishing machine with two polishing sub-units with a wet ISMS integrated in the machine.

A further embodiment of the apparatus is shown in FIG. 3. In FIG. 3, polishing unit 14 comprises at least two polishing sub-units 26. Sub-unit 26a runs a selective process with slurry designed to efficiently remove and planarize copper. Sub-unit 26b runs a non-selective process designed to uniformly remove copper, barrier and dielectric (a '1:1:1 process' in the terms of the art).

In one embodiment of a method for employing the apparatus of FIG. 3, transport system 22 takes the wafer to polishing sub-unit 26a first. Sub-unit 26a removes most of the top layer of copper that is above the dielectric damascene structure, and substantially planarizes the surface. Ideally, sub-unit 26a does not polish enough to break through to the barrier layer. Transport system moves the wafer to the ISMS, which measures the planarization of the top copper surface so that sub-unit 26a can be controlled for subsequent wafers. The transport system transports the wafer to polishing sub-unit 26b, which finishes the polishing of the wafer, and then to the ISMS to characterize dishing, erosion, and residue so that the whole process for subsequent wafers can be controlled. Finally, the transport system 22 takes the wafer to the exit wafer carrier 18.

In another embodiment of the method using the apparatus in FIG. 3, the ISMS measures the thickness of the remaining copper after sub-unit 26a has removed most of the copper. This measurement is then the basis to control both the low selectivity polish step for the current wafer on sub-unit 26b and the high selectivity polish of subsequent wafers on sub-unit 26a.

Figure 4:
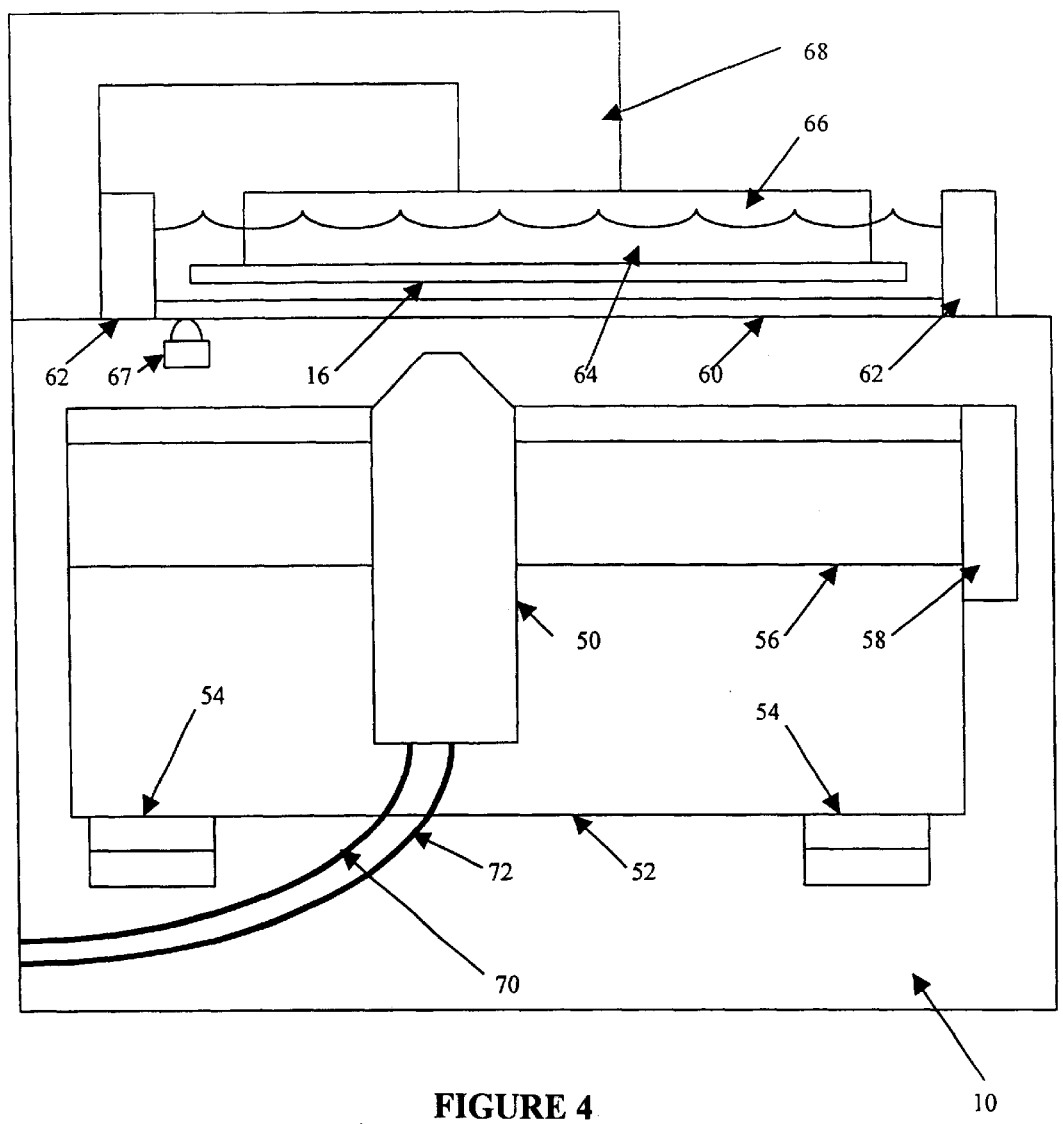
FIG. 4 is the side view of an embodiment of a wet ISMS.
Figure 5:
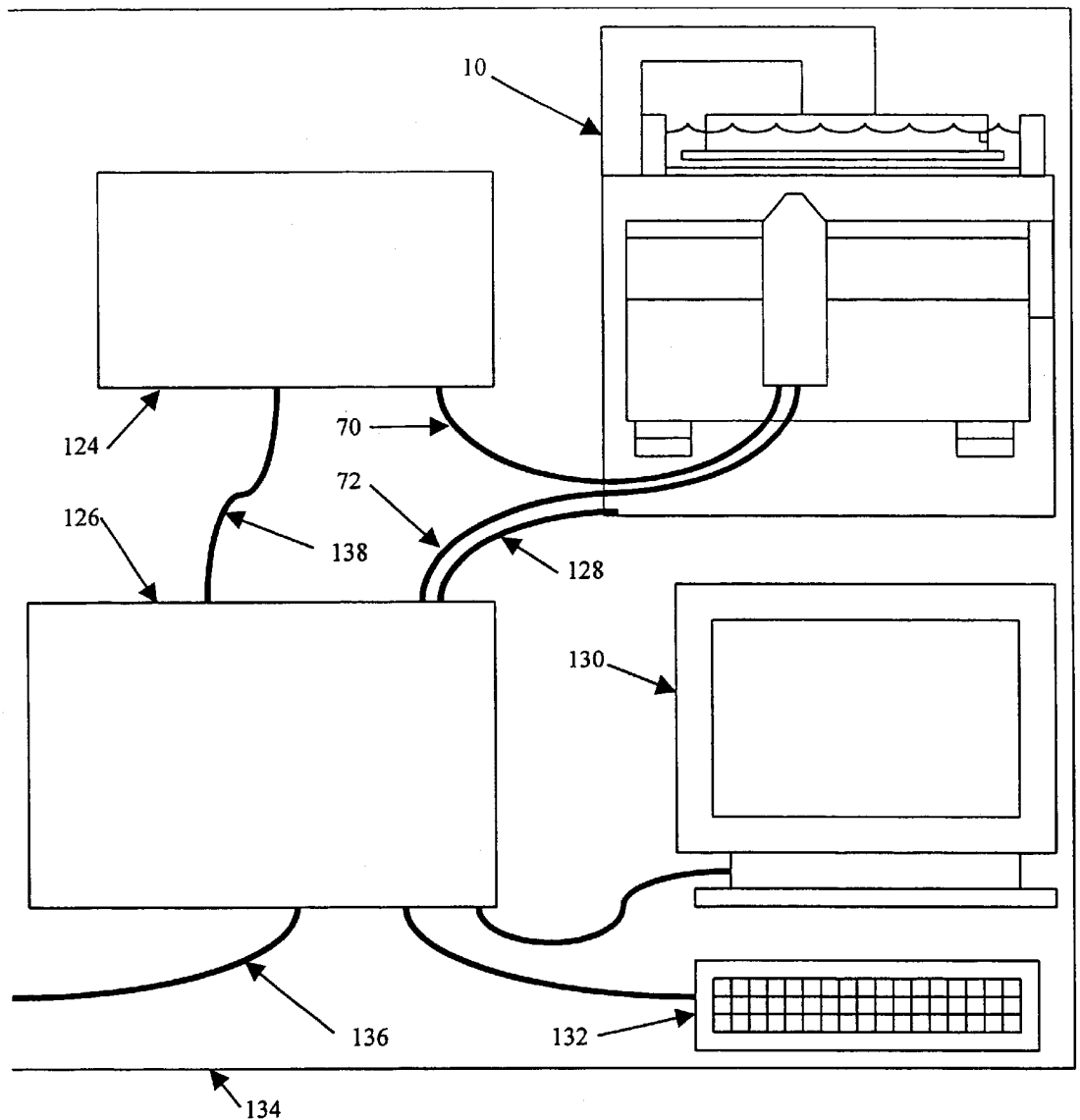
FIG. 5 is a schematic representation of an ISMS system, including the ISMS itself and supporting components.

FIG. 4 shows an embodiment of ISMS 10 intended for measuring wet wafers. The main component of ISMS is optical assembly 50, described in detail below. The optical assembly is supported by back plane 52, y-stages 54, x-stage 56, and x drive motor 58. The optical assembly "looks at" wafer 16 through window 60 and water 64 which is contained in tank 62. Chuck 66 supports the wafer, and gantry 68 raises and lowers the wafer into the water so that transport system 22 (not shown) can place and retrieve the wafer 16 in the ISMS 10. Preferably, the chuck can rotate to aid in aligning the wafer in conjunction with edge sensor 67 to detect the edge of the wafer and the location of the wafer's notch. FIG. 5 shows ISMS system 134 comprising ISMS 10, optical fiber 70, electrical cables 72, light box 124, controller 126, controller cables 128, monitor 130, and keyboard 132.

Referring to FIG. 4 and FIG. 5, optical fiber 70 brings light to optical assembly 50 from light box 124. Electrical cable 72 carries power from controller 126 to optical assembly 50, and conducts signals back and forth between controller 126 and optical assembly 50. Communication link 136 conveys information between the polishing machine or factory and the ISMS regarding the wafers to be measured and the measurement results.

In FIG. 4, the primary function of the ISMS is to scan optical assembly 50 in x and y directions so that the surface of wafer 16 can be inspected. Back plane 52 supports optical assembly 50, x-stage 56, and x-motor 58, all of which move in the y-direction, perpendicular to the plane of the figure, driven by the y drive motor (omitted for clarity). X-drive motor 58 drives optical assembly 50 on x-stage 56 in the x-direction, ie, horizontally in the figure. Water 64 is necessary to keep the wafer wet and provide a homogeneous medium through which the wafer can be inspected. Tank 62 and window 60 contain water. Window 60 is necessary to protect the optical assembly and mechanical assemblies from water 64 and wafer 16 from particles generated by the mechanical assemblies, and simultaneously to allow optical assembly 50 to see wafer 16. Gantry 68 preferably raises and lowers wafer 16 into water 64 with a tilting motion, so that no portion of the wafer is horizontal while its lower surface is entering the water. The electronics subassembly includes controllers, preferably including a microprocessor to control aspects of the operation of the system.

Referring to FIG. 5, the ISMS system 134 provides electrical and optical power to the ISMS 10, as well as control signals and an outlet for its measurements, and an information pathway to the polishing machine or factory. Light box 124 preferably contains a xenon arc-lamp with focusing optics to provide light to fiber 70, a shutter, and selectable filters. Controller 126 acts to manipulate shutter and selectable filters via light-box control cables 138. In alternative embodiments, the lamp may be a tungsten-halogen lamp, or a deuterium lamp, or at least one laser.

Figure 6:
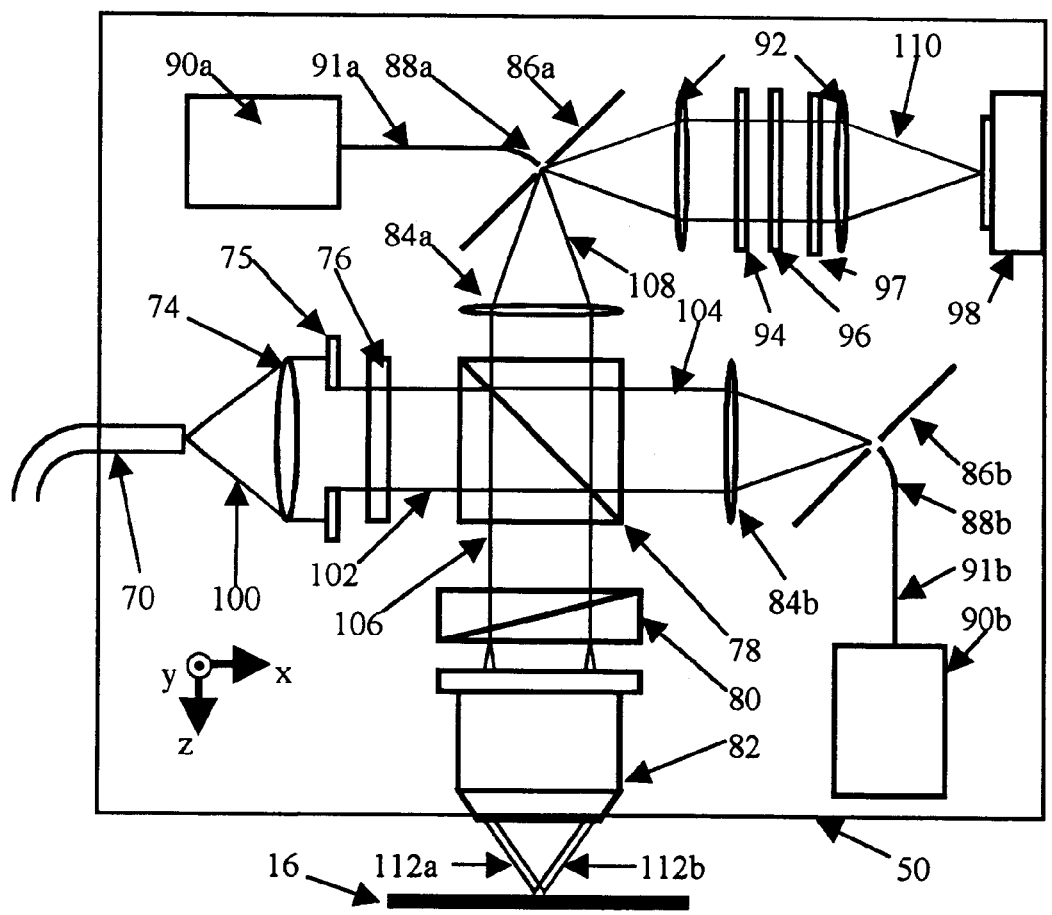
FIG. 6 is a schematic representation of an optical assembly for the ISMS incorporating a QDIC, NIR, and imaging system.

FIG. 6 shows an embodiment of optical assembly 50, inverted with respect to the embodiment of the ISMS shown in FIG. 4. This embodiment of the optical assembly comprises three subsystems: a quantitative differential interference contrast microscope (QDIC) as described by Hong et al. as an optical profiler; a normal-incidence, dual-beam reflectance spectrometer (NIR); and an imaging subsystem. Elements common to all subsystems are source fiber 70, aperture 75, beam splitter 78, objective 82, imaging lens 84*a*, and pinhole mirror 86. The imaging system further comprises re-imaging lenses 92, and camera 98. The camera is preferably a charge-coupled device (CCD) camera. The QDIC comprises: polarizer 76; birefringent prism 80; compensator 94; rotating analyzer 96 and bandpass filter 97 in addition to the common components and the imaging system's components. The NIR comprises the common components and the pinholes 88, spectrometer fibers 91, spectrometers 90, and monitor imaging lens 84*b*. The components labeled "a" in FIG. 6 are generally related to the sample channel of the spectrometer, and the "b" components to the monitor channel.

In FIG. 6, fiber 70 brings light to the optical assembly 50 from a white light source, preferably a xenon lamp. The light source emits a light cone 100. The lamp is housed remotely in light box 124, as discussed above, to prevent it from heating the optical assembly. Light cone 100 is collimated by collimator 74 to produce source beam 102, which is stopped down by aperture 75. Polarizer 76 is on a flipper (not shown) to allow it to be alternately in or out of source beam 102. Beam splitter 78 splits source beam 102 into monitor beam 104 and sample beam 106, which is directed towards the sample. Birefringent prism 80 is on a flipper (not shown) so that it can be either out of sample beam 106 for NIR and imaging functions or in the sample beam for QDIC functions. Prism 80, preferably a Nomarski prism, is mounted so that controller 126 can rotate it about a z-axis to predetermined positions for reasons discussed below. Objective 82 focuses the sample beam onto the sample and then collects the light reflected from the sample. A reflected beam retraces the path the of the sample beam up to beam splitter 78, where it continues on to imaging lens 84*a*. The imaging, lens focuses the reflected beam onto pinhole mirror 86*a*. Pinhole 88*a* passes a sample of the reflected beam to spectrometer fiber 91*a*, from where it proceeds to the spectrometer to be characterized. The pinhole mirror reflects the remainder of the reflected beam into the image beam 110, which is focused by re-imaging lenses 92 onto camera 98 to produce an image of wafer 16. Compensator 94 is preferably a quarter-wave plate. Analyzer 96 is mounted so that it can be rotated to specific positions by controller 126. Preferably, filter 97 is wavelength selectable.

The QDIC is the preferred embodiment of an optical profiler for the ISMS. Its operation is described by Hong et al, (see below) which is incorporated in its entirety by reference. Additional details are found in Corle, Lessor, Hartman, and the Handbook of Optics (see below). Polarizer 76 and birefringent prism 80 break the sample beam 106 into two distinct sheared beams 112 which are separated by a shear distance in x at the sample, and have orthogonal polarization vectors: one has polarization in the x-direction and the other in the y-direction. The sheared beams are reflected from the wafer, acquiring different phase and amplitude shifts indicative of the profile and characteristics of the surface, as discussed in detail below. The sheared beams combine coherently in birefringent prism 80 to form a single reflected beam 108. The coherent interaction of the two beams has an unknown polarization, amplitude and phase depending on the form of the sample, i.e., its reflection coefficients and topography. Compensator 94 with its fast axis at 135° in the x-y plane converts the two components of the image beam 110 into left and right rotating polarized components with phases determined by the reflection coefficients. Filter 97 limits the spectrum of light to a narrow band, preferably 25 nm around a predetermined wavelength, preferably 550 nm. At analyzer 96, the two circularly polarized components are combined and a resulting intensity is imaged onto camera 98. The ISMS collects four intensity images for differing rotations of the analyzer 96 to calculate the relative phase of the two beams. With analysis described below, this yields a single differential phase image, $\Delta\Psi(x,y)$ at the wavelength corresponding to filter 97, as discussed below.

Figure 7:
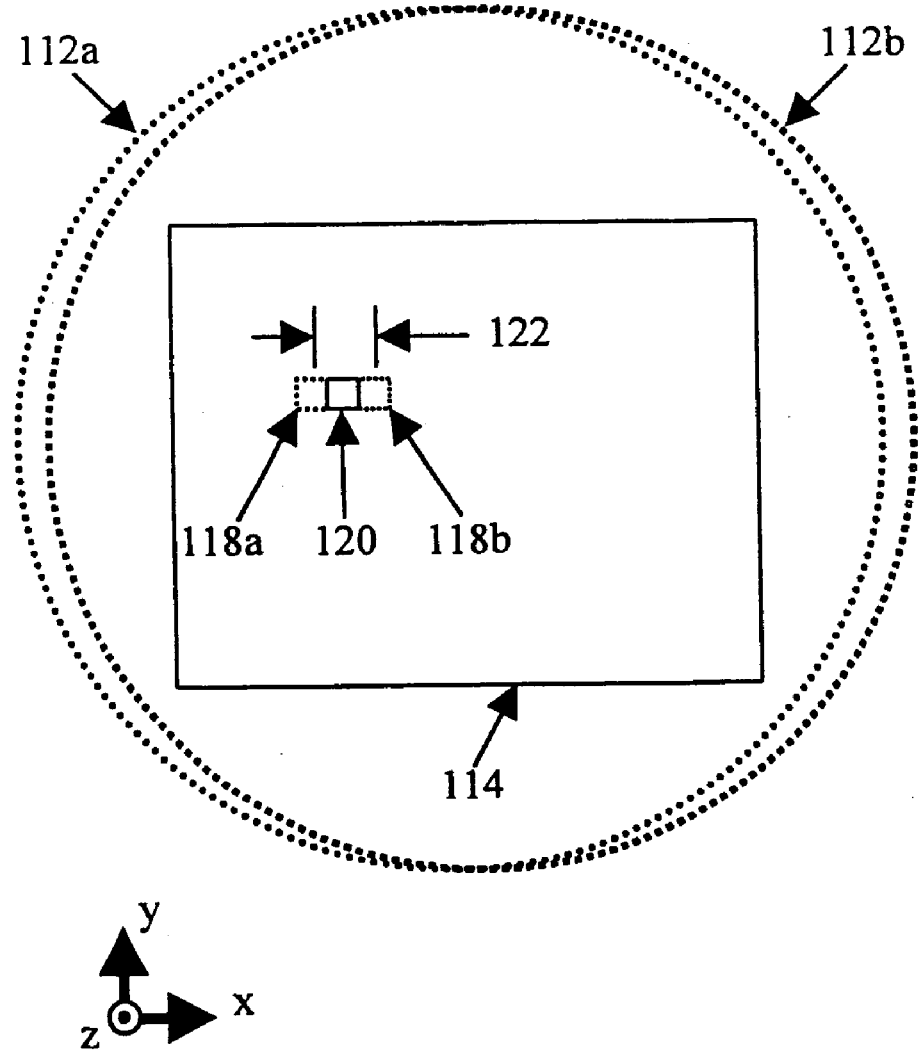
FIG. 7 is the top view of the wafer in the region being inspected by a QDIC.

It is noteworthy that FIG. 6 has been distorted for clarity with regard to the sheared beams. FIG. 7 more accurately show how the sheared beams 112 image a field of view 114. The two sheared beams 112 illuminate two circular fields, preferably about 1.6 mm in diameter. Sheared beam 112*a* has x polarization and sheared beam 112*b* has y polarization. The field of view 114 is the image of the camera back through the optics onto the wafer. The illumination optics, imaging optics and camera are configured so that every pixel of the camera receives illumination from both beams. A typical pixel from the camera that images back onto the wafer as patch 120 receives light from shear patches 118. Shear patch 118*a* contributes light to the pixel from sheared beam 112*a*, and shear patch 118*b* contributes light to the pixel from sheared beam 112*b*. Thus, each pixel receives two contributions of reflected light coming from patches on the wafer separated by the shear distance, $\Delta x$ 122. The shear distance and pixel size have been exaggerated in the figure for clarity. The shear distance, $\Delta x$, is preferably equal to the pixel pitch, $\Delta X$, imaged onto the wafer, which is preferably about 2 microns. However, $\Delta x$ and $\Delta X$ need not be equal.

Figure 16:
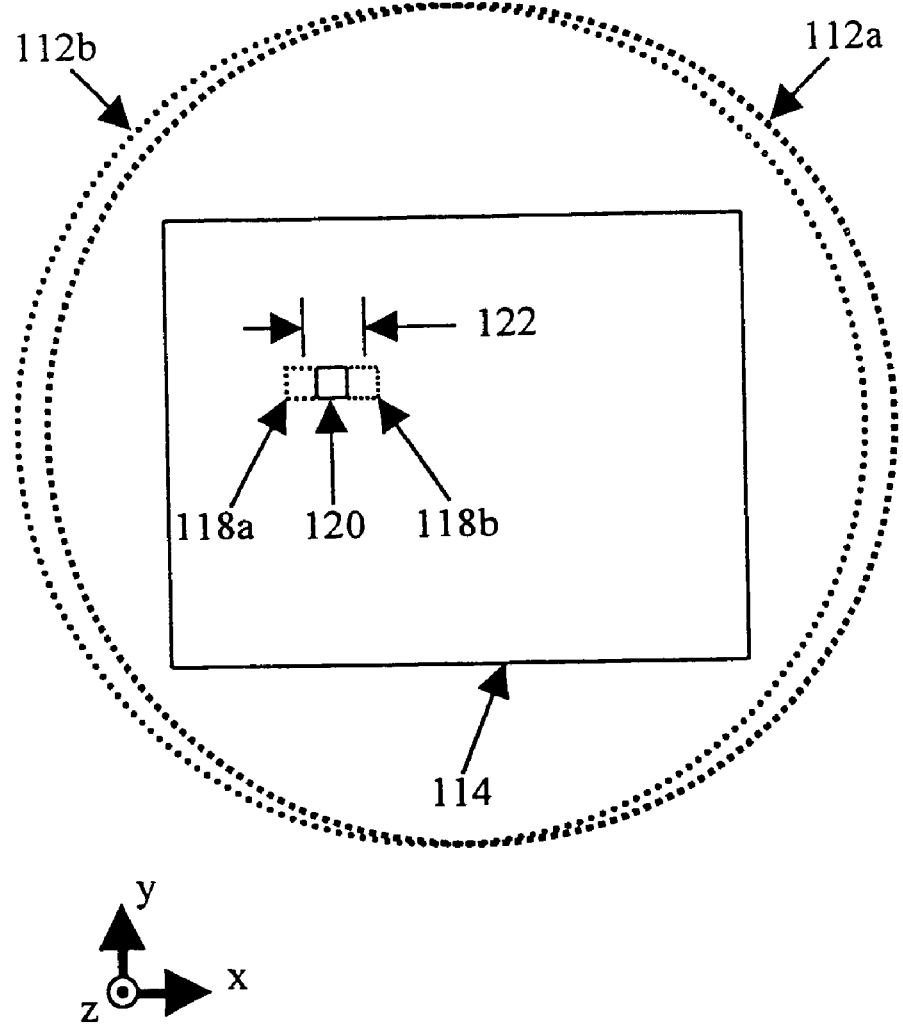
FIG. 16 is the top view of the wafer in the region being inspected by a QDIC, with the birefringent prism rotated 180°.
Figure 17:
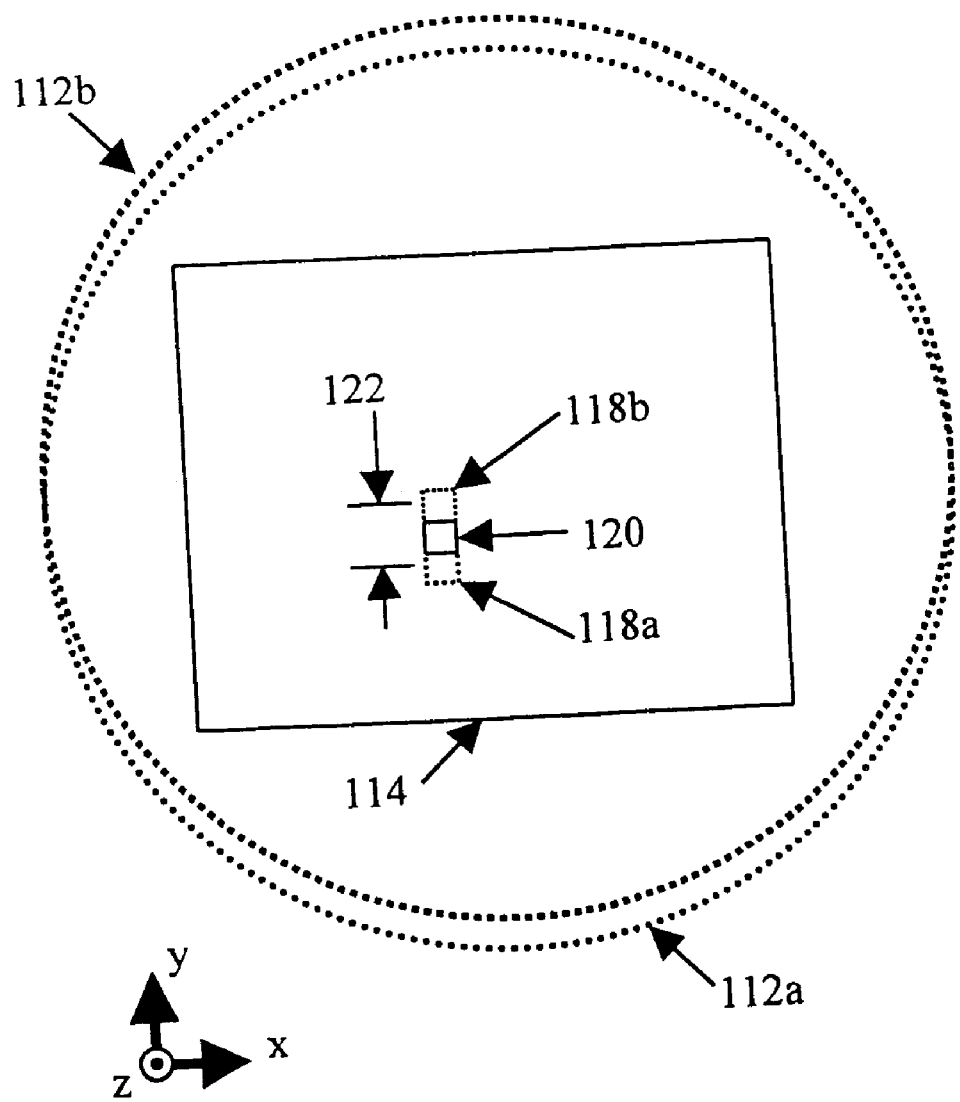
FIG. 17 is the top view of the wafer in the region being inspected by a QDIC, with the birefringent prism rotated 90°.

According to the invention, birefingent prism 80 rotates about the z-axis. Rotating the prism 180° exchanges the positions of sheared beams 112*a* and 112*b*, as shown in FIG. 16. This is useful to compensate for some samples as discussed below. With the shear direction aligned with the x-axis, as shown above, the QDIC makes profiles in the x-direction. Rotating the prism 90° rotates the shear direction to the y-axis, as shown in FIG. 17, and allows the QDIC to profile in the y direction. It will be readily appreciated that rotating prism −90° exchanges the positions of the two shear beams in the y-direction.

Figure 8:
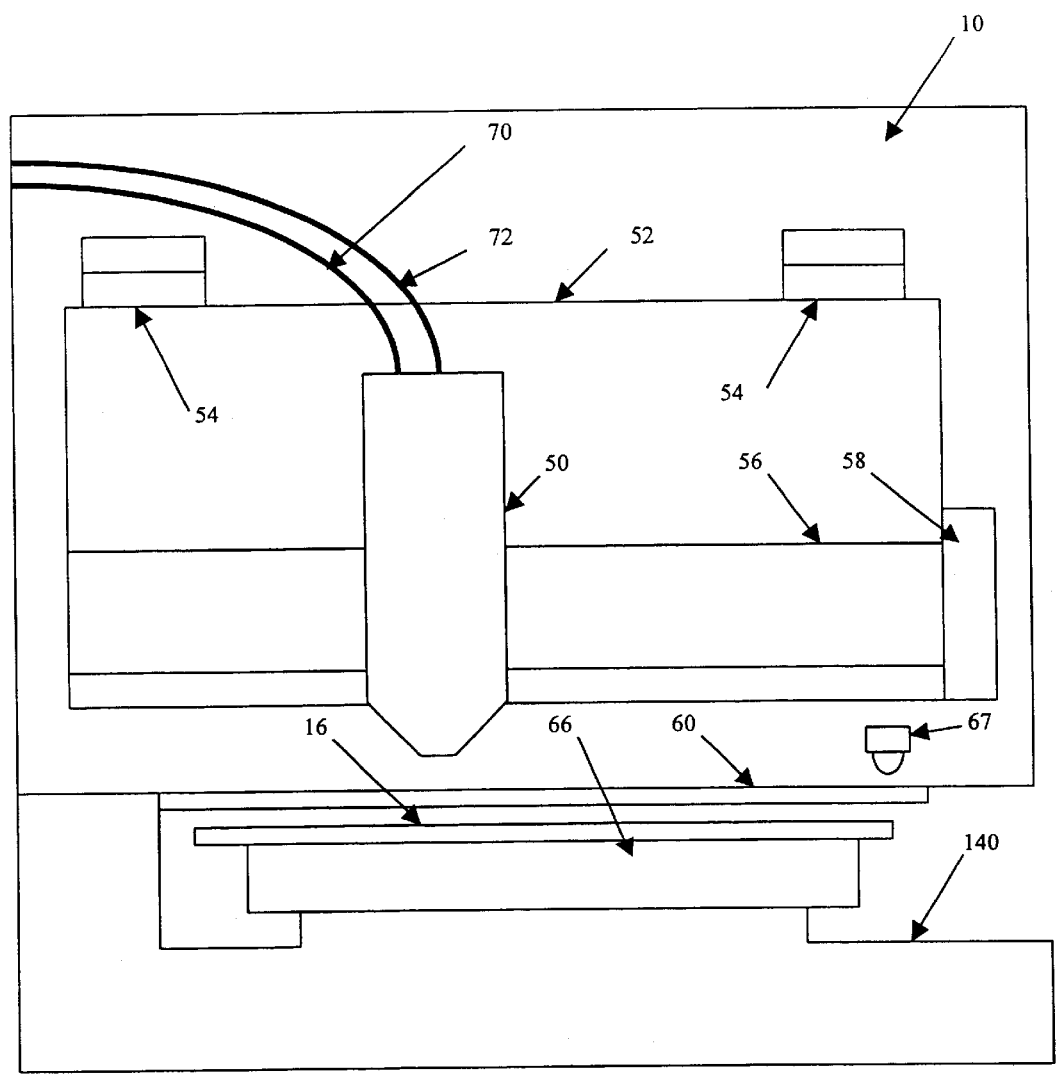
FIG. 8 is the side view of an embodiment of a dry ISMS.

FIG. 8 shows an embodiment of the ISMS 10 intended for measuring dry wafers, in an alternative to the embodiment in FIG. 4 for measuring wet wafers. The ISMS is inverted with respect to the earlier embodiment and components for water containment are replaced with respect to the earlier embodiment by support chassis 140. Window 60 has been retained relative to the earlier embodiment to protect the top surface of wafer 16 from particles generated by the components inside the ISMS, eg, the y-stages 54 and the x-stage 56.

It can be readily appreciated that many alternative embodiments for the ISMS are possible for both wet and dry operation, while the embodiments discussed above are preferred embodiments. In other embodiments, the wafer may be held vertically by a chuck or clamps during measurement and the remainder of the ISMS rotated to accommodate the alternative wafer position. While preferred embodiments of the invention position optical assembly 50 to inspect a predetermined position on wafer 16 by moving the optical assembly in x and y, alternative embodiments may also move the wafer. Specifically, the wafer may be translated or rotated. In a specific embodiment, the ISMS may rotate the wafer and translate the optical assembly in one direction at least over a radius of the wafer. In this embodiment, the optics translate somewhat more than a radius of the wafer in one direction, and a small amount in the orthogonal direction, to allow for placement uncertainty of the wafer onto chuck 66 by transport system 22. Other alternative embodiments can move the optical assembly with an (r−θ) translation system. In the embodiment shown in FIG. 4, the wafer is immersed in water. In alternative embodiments, the ISMS maintains a column of water between objective 82 and wafer 16. In such embodiments, the final lens in the objective 16 (the one closest to the wafer) seals the optics from the water, and window 60 is removed.

Figure 9:
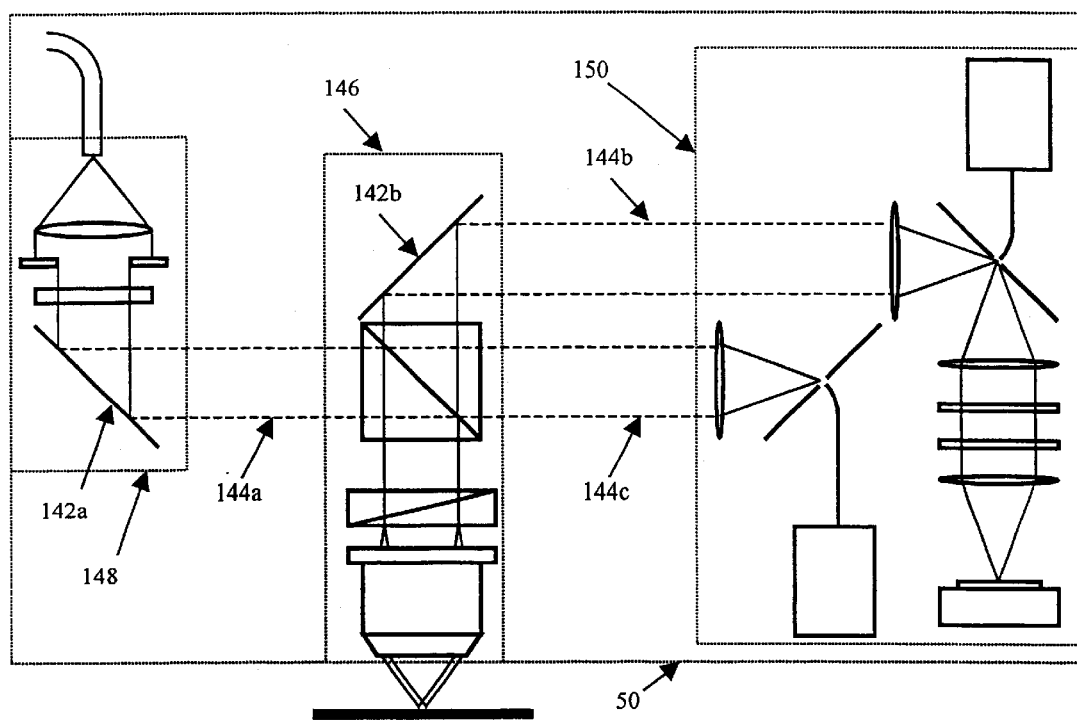
FIG. 9 is the side view of schematic representation of the optical assembly of an ISMS with a QDIC and NIR employing one-dimensional scanning optical paths.

In the embodiments of FIGS. 4 and FIG. 8, optical assembly 50 is translated as a unit. Alternative embodiments may fix selected components in one or two dimensions, and translate others in one or two dimensions. Examples of such systems are disclosed in U.S. Pat. Nos. 5,517,312 and 5,764,365. One such embodiment is shown in FIG. 9. In FIG. 9, illumination subsystem 148 provides light to objective assembly 146 via turn mirror 142a and collimated beam 144a. Detection subassembly contains the detection optics and electronics for both the sample and monitor beam 144b and 144c, respectively, which emanate from objective assembly 146. Turn mirror 142b turns the sample beam 144b parallel to monitor beam 144c.

Beams 144 are collimated beams allowing translation of the hardware components at either end of the beam. In this embodiment, illumination subsystem 148 and detection subsystem 150 are fixed to back plane 52, and scan in the y-direction, perpendicular to the plane of the figure. Objective subsystem 146 scans on back-plane 52 in the x-direction, and moves with it in the y-direction. Turn mirror 142a allows the generally vertical orientation of illumination subsystem 148, for space considerations. Equivalently, additional or other turn mirrors may be inserted to allow space-efficient packaging of the subsystems in further embodiments.

Figure 10:
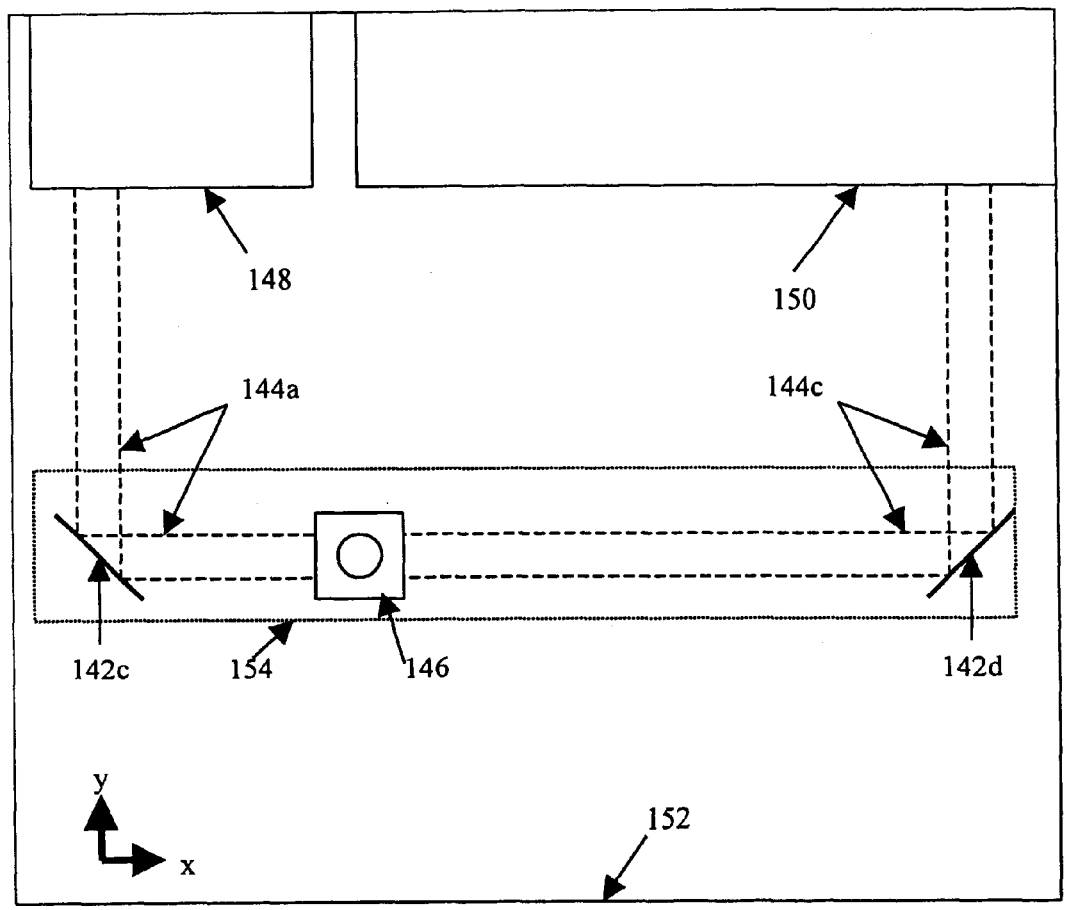
FIG. 10 is the top view of schematic representation of the optical assembly of an ISMS with a QDIC and NIR employing two-dimensional scanning optical paths.

An alternative embodiment is illustrated in FIG. 10, which illustrates the components of the ISMS as viewed from the wafer. Illumination subassembly 148 and detection subassembly 150 are fixed to ISMS chassis 152. Translation subsystem 154 translates in the y-direction and comprises turn mirrors 142c and 142d and objective assembly 146. Objective assembly 146 translates in the x-direction along translation subsystem 154. Collimated beam 144a provides light to objective subsystem assembly 146 from the illumination subsystem. Collimated beam 144c is the monitor beam propagating from objective assembly 146 to detection subsystem 150. Collimated beam 144b is below beam 144c in FIG. 10, thus it is not shown in the figure. However, it is the sample beam from objective subsystem 146 to detection subsystem 150.

Figure 11:
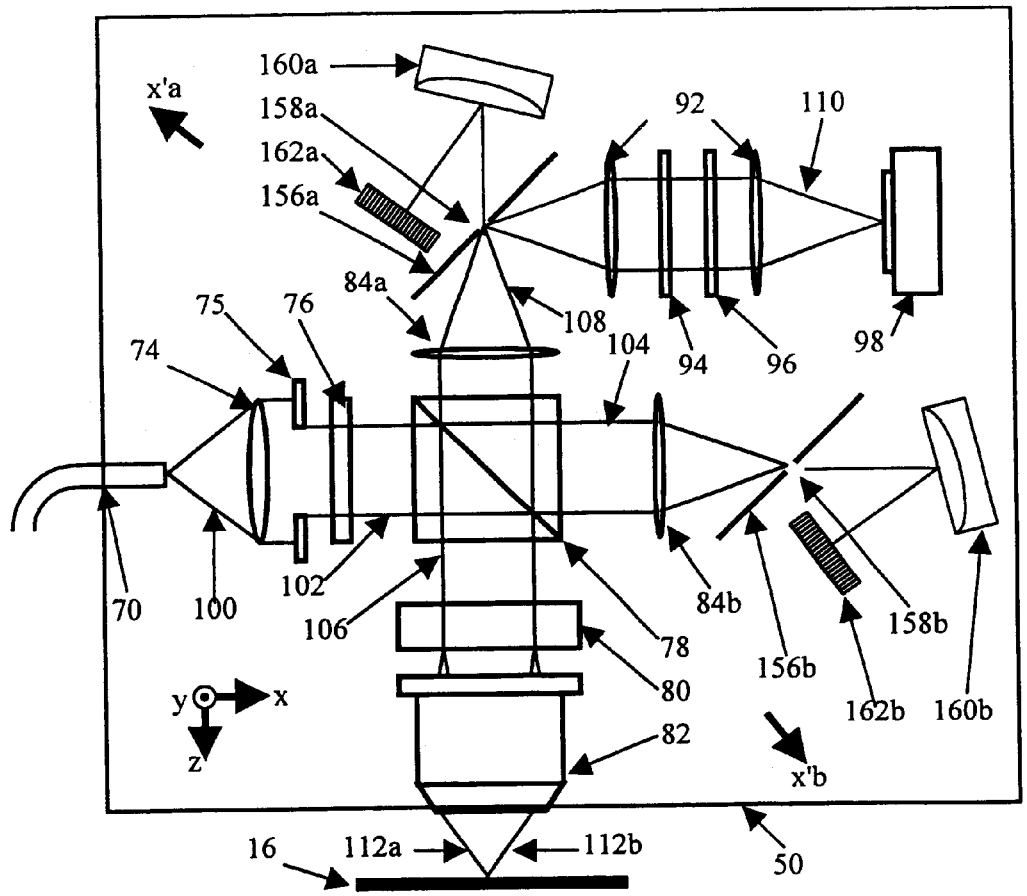
FIG. 11 is the side view of an optical assembly employing QDIC, INIR, and imaging system.

FIG. 11 shows an alternative embodiment for optical assembly 50 which allows for n imaging NIR (INIR). In this embodiment, birefringent prism 80 has been rotated 90° so hat the shear direction for the QDIC is in the y-direction, and thus sheared beams 112 cannot e distinguished in the view of the figure. Pinhole mirrors 86 and pinholes 88 have been replaced by slit mirrors 156 and slits 158. Spectrometers 90 and spectrometer fibers 91 in other embodiments have been replaced in this embodiment by diffraction gratings 160 and detector arrays 162. Slits 158s have their long directions perpendicular to the plane of the figure, so that they are not visible as slits. Dectector arrays 162 are two-dimensional, and preferably are CCD cameras. Diffraction gratings 160 focus light passing through slits 158 onto detector arrays 162 such that position along the slits in y is imaged into position in y on detector arrays 162, and wavelength of light λ varies along directions x' of arrays 162. The components labeled 'a' belong to the sample channel, and the components labeled 'b' belong to the monitor channel. It is apparent that for this embodiment the x and y axes have been switched relative to other embodiments.

Figure 30:
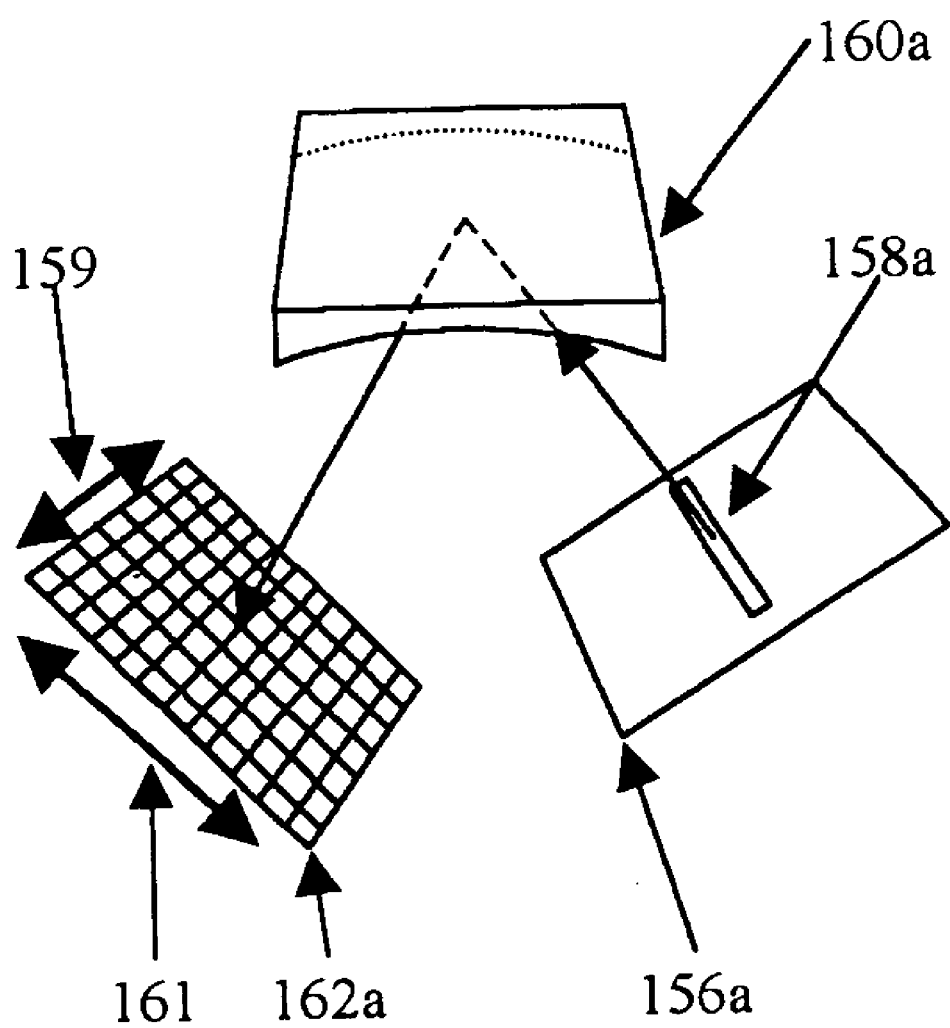
FIG. 30 illustrates the components of an imaging spectrometer in perspective. The top of the grating is visible. It reflects light from its lower surface down and to the left.

FIG. 30 shows the spectrometer components in the INIR in perspective. Slit 158a in the slit mirror 156a is greatly elongated in the y-direction in the figure. Light emanating from propagates up to the diffraction grating 160a and strikes its lower. Grating 160a reflects light downward and to the left towards two-dimensional array 162a. It focuses the slit onto two-dimensional array 162a in one direction and splits the light into wavelengths in the other direction. On the array, wavelengths vary in wavelength direction 161, and imaged y-position from the wafer is imaged along image direction 159.

Figure 33:
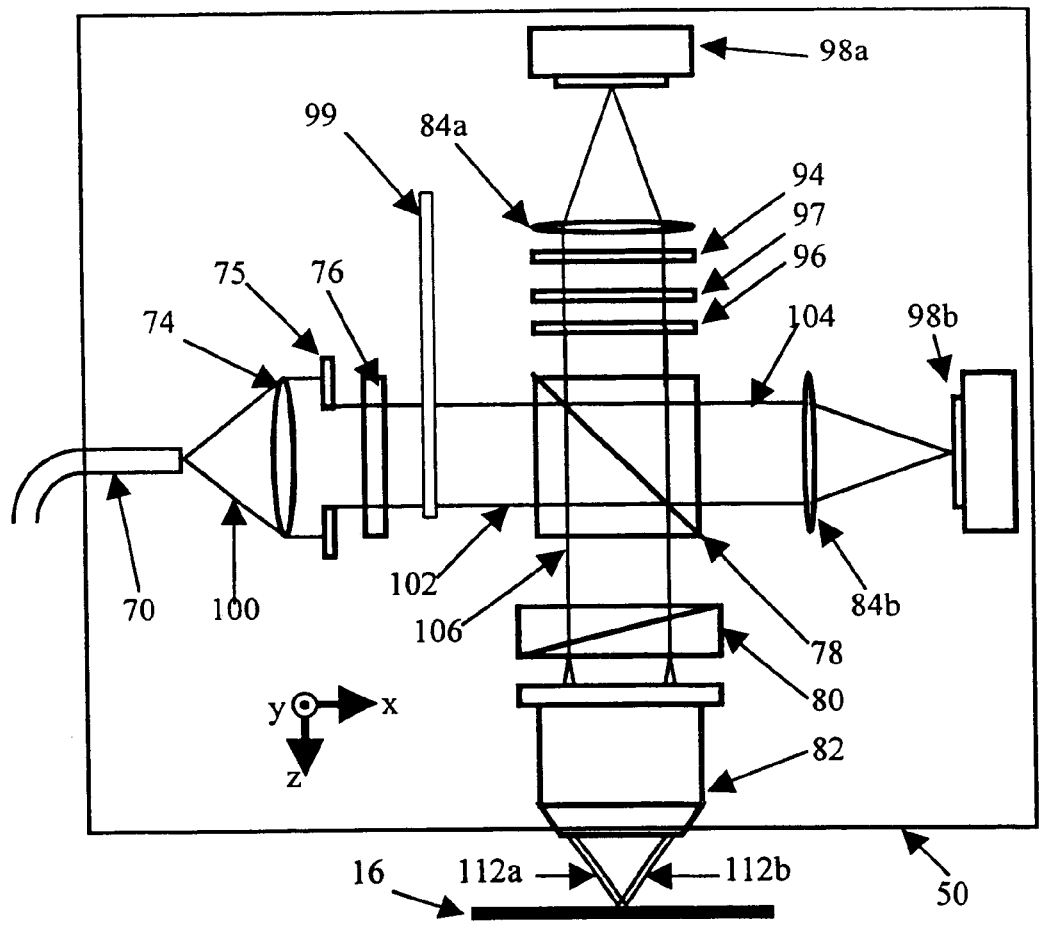
FIG. 33 is the side view of an optical assembly employing QDIC, and an alternative INIR.

FIG. 33 is the side view of an optical assembly employing QDIC, and an alternative INIR. FIG. 33 shows an alternative embodiment for optical assembly 50 with a different type of INIR. In this embodiment the spectrometers and pinhole mirrors have been replaced by a variable filter 99 and cameras 98a and 98b. Variable filter 99 is preferably a filter wheel. It controls the wavelength of light λ being imaged by cameras 98. The cameras acquire a sequence of images as the variable filter 99 changes the wavelength. The result is a spectrum at each pixel in the cameras. Camera 98b is a monitor camera to sample the intensity of light coming through filter 99. In other embodiments it is replaced by a simple detector (instead of a camera), or altogether absent. In this embodiment the INIR can serve the purpose of an imaging system, eg, for pattern recognition.

The methods of applying the ISMS are appropriate for inspection of several types of surfaces. Since the ISMS is an optical instrument, the interactions of light with surfaces are important for its operation. In general, surfaces in microelectronics manufacture are layered. Some of the layers are transparent and others are opaque. As appreciated by one skilled in the art, materials below a transparent layer surface substantially affect light reflected from the transparent layer. In contrast, any material below an opaque layer insubstantially affects light reflected from the opaque layer. A stack of layers is all of the layers from the top surface of the wafer down to the top of the first opaque layer, which is the stack substrate. In some cases the stack substrate will be the silicon wafer, but not in all cases. At each point on the surface of the wafer in the field-of-view of the instrument, (x,y), there is a stack, which has an optical, complex reflection coefficient r(x,y). The complex reflection coefficient, r(x,y), is a function of angle of incidence, wavelength, and polarization of light. They are determined by the specific design of the instrument. For best results, the wavelength dependence of optical parameters is taken into account.

A homogeneous surface is an area such that the stack at every point (x,y) is the same stack: the optical properties and thickness of the layers in the stack are identical. In this case r(x,y) will be the same for the whole area. In practice a homogeneous surface will have the same simple stack everywhere in the field of view. A simple stack is a stack with no layers between the ambient medium and the stack substrate. Thus, the reflection coefficient for a simple stack depends only on the optical properties of the stack substrate, and not on its thickness or any properties of the underlying layers. Many optical texts teach how to calculate the reflection coefficient for a simple stack, eg, Jellison (see below).

Figure 14:
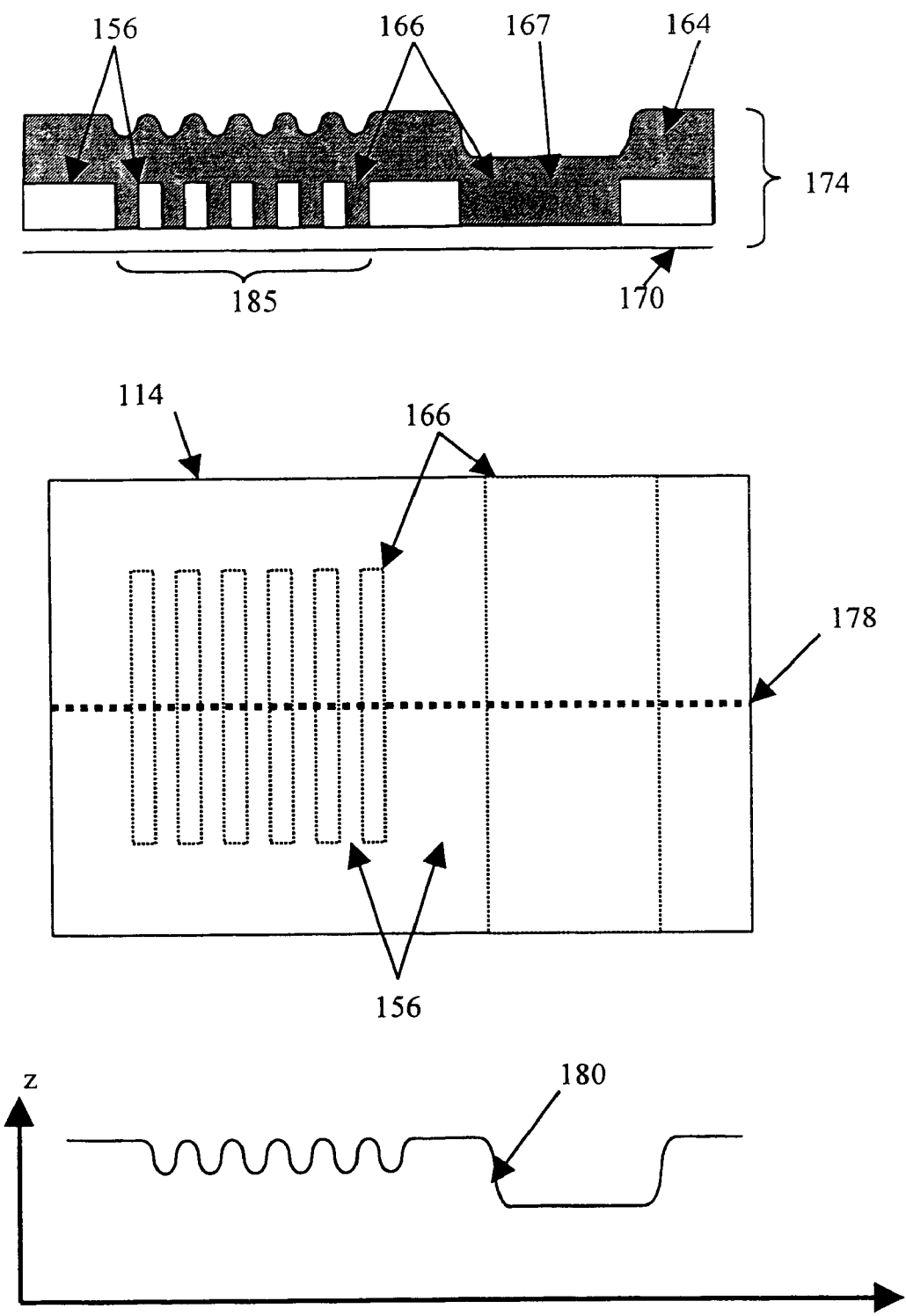
FIG. 14 illustrates side and top views of a homogeneous surface, and a profile of the surface.

An example of a homogeneous surface is shown in FIG. 14. It is a portion of wafer 16 in field-of-view 114 after electro-deposition of copper 164. There is underlying structure 170, upon which rests dielectric spaces 156. Copper fills lines 166 between the spaces. There is wide line 167 and array 185 of narrow lines. Looking down from above, only copper is visible. The copper surface along scan line 178 has profile 180. The profile is the relative height of the surface at multiple points. In principal, two points would constitute a profile. However, surfaces are in fact tilted, and two points do not allow tilt to be distinguished from profile. Thus, at least three points are required to produce a profile with any tilt removed. Such a profile is termed a leveled profile. Profile 180 in FIG. 14 is a leveled profile.

Figure 15:
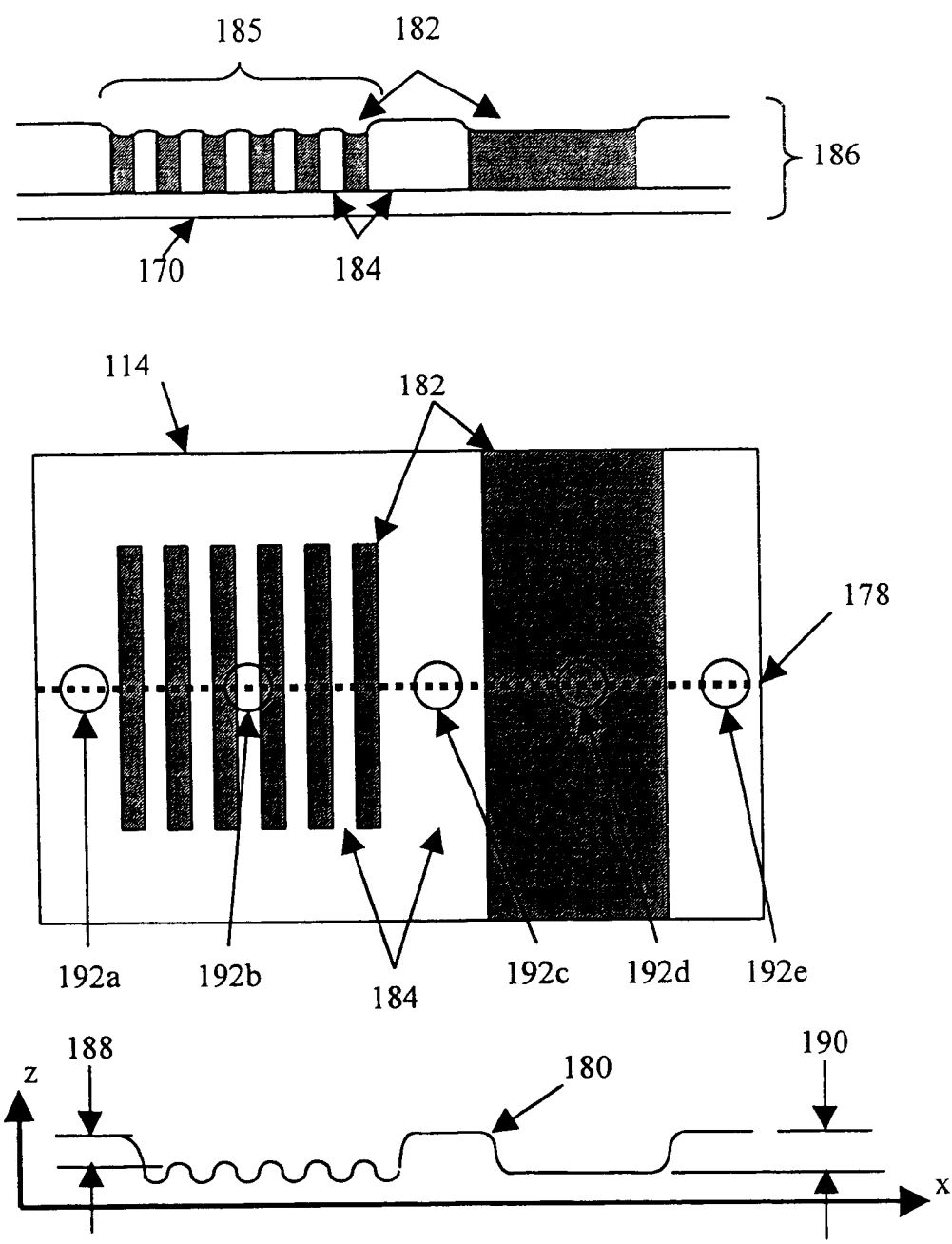
FIG. 15 illustrates side and top views of a heterogeneous surface, and a profile of the surface.

A heterogeneous surface is an area such that r(x,y) is not constant. FIG. 15 shows an example of a heterogeneous field-of-view. It is a portion of wafer 16 in field-of-view 114 after polishing of copper 164. Underlying structure 170 is shown, upon which rests polished dielectric spaces 184. Copper fills the polished lines 182 between the dielectric spaces. When viewed from above with an instrument having measurement spot 192, different points (x,y) have different reflection coefficients r(x,y). This field of view has thee types of stacks. Spot 192d sees a simple stack, ie, copper only. Spots 192a, 192c and 192e see locally uniform stacks. Spot 192b sees an array or grating stack, if the pitch is presumed smaller than the spot size. Field of view 114 in FIG. 15 is heterogeneous since there are different types of stacks within the field-of-view and since areas of uniform stacks or grating stacks will not be homogeneous, as discussed below.

A uniform stack is an area where there is the same number of layers of the same materials everywhere. The thickness and properties of the layers may vary slowly, ie, on a scale greater than an instrument's spot size. In fact, the reflection coefficient of a uniform stack r(x,y) is a function of the layers' thickness and other properties. Thus, a uniform stack is a heterogeneous surface. As described above, spots 192a, 192c and 192e in FIG. 15 see a uniform stack. Many optics texts teach how to calculate the reflection coefficient for uniform stacks based on the thicknesses of the layers and the optical properties of the layers, ambient medium and stack substrate, eg, Jellison (see below).

A grating stack is a stack in which at least one layer in the stack has regions of alternating materials on a scale finer than the spot size. Thus, an array is distinguished from a uniform stack that has no significant local lateral variation. Array 185 in FIG. 15 is a grating stack. The array will cause diffraction of the light. The effective reflection coefficient over an array will include the effects of any diffraction orders that are detected by the optics. The effective reflection coefficient from a grating stack will depend on its detailed geometry and optical properties of the array, as taught by Niu and Li (see below). In practice a grating stack is a heterogeneous area since thickness of layers and array geometry vary from point to point.

Hong (see below) teaches data collection and processing with the QDIC to obtain a phase image. First, four intensity images $I_1(x,y)$, $I_2(x,y)$, $I_3(x,y)$ and $I_4(x,y)$ are collected with four positions of the analyzer separated sequentially by 45°. A phase difference image is calculated as $$\Delta\psi(x_i, y) = \tan^{-1}\frac{I_4(x, y) - I_2(x, y)}{I_1(x, y) - I_3(x, y)}. \tag{1}$$

Each pixel in the QDIC image represents the difference in phase of the reflected light from the two patches on the wafer separated by the shear distance, as described for one pixel in connection with FIG. 7. The shear distance, $\Delta x$ 122, is substantially uniform over field-of-view 114. Thus dividing each pixel in the phase difference image $\Delta\Psi$ by $\Delta x$ yields a finite-difference approximation to the x phase derivative. A phase image of the wafer can be approximated by cumulative sums:

$$\psi(x_i, y) = \sum_{j=0}^{i} [\Delta\psi(x_j, y)/\Delta x]\Delta X + \psi(0, y) - \psi_0(x_i, y). \tag{2}$$

where $\Psi_0(x_i,y)$ is a reference phase resulting from a QDIC measurement on a reference flat, and $\Psi(0, y)$ is an unknown constant of integration for each line (y value) in the image. Thus the 'phase image' produced by the QDIC is in fact a set of phase profiles in x. The relative heights of the x-profiles are not known without further information, as discussed below. The phase profiles from the QDIC are immune to vertical vibrations that change the distance between the optical assembly 50 and the wafer 16, because it is a common-path interferometer. The two sheared beams 112 traverse the same distance from the optics to the wafer. If this distance changes due to vibration, it changes the same amount for both shear beams and therefore does not affect the phase difference between them that is recorded by the QDIC. This is one critical property of the QDIC as the preferred optical profiler for the ISMS 10 since the profile resolution for the ISMS is of the order of nanometers. The QDIC is as sensitive to lateral vibration (in the x and y directions) as any imaging system of comparable lateral resolution. Since the pixel pitch is of the order of microns, lateral vibration is not problematic to the technique.

According to the invention, the ISMS measures physical profiles of the samples being inspected, ie the relative position of the top surface of the wafer at a set of two or more points. As described, interferometric profilometers such as the QDIC measure phase profiles. It is an aspect of the invention to provide a method to convert phase profiles into height profiles for heterogeneous surfaces.

Phase profiles result from two physical contributions:

$$\Psi(x,y) = \Psi_r(x,y) + \Psi_p(x,y),$$

where $\Psi_r$, the reflection phase, is the phase of the reflection coefficient r(x,y) referred to the phase of the incident light at the top surface of the sample, and $\Psi_p$ is the topographic phase determined by the height profile of the sample. The reflection phase at a point is controlled by the stack at the point, in addition to the wavelength, polarization and the angles of incidence and detection. The topographic phase is the two-way propagation phase between the actual surface and a reference surface, which is the location of the optical flat that produced the reference phase in Eq. (2). If the height of the surface is h and light is normally incident, the topographic phase is $$\Psi_p = 4\pi h/\lambda, \quad (3)$$

where, $\lambda$ is the wavelength of the light in the ambient medium (air or water), and the time-dependent phase of light as $e^{-i\alpha x}$ is suppressed. In practice $\lambda$ is an effective wavelength of a spectral band of light, preferably controlled by a filter in the ISMS's 10 light box 124 that is in place during QDIC measurements. In other embodiments, it may be the effective wavelength of a laser. Those skilled in the art will recognize that Eq. (3) can be modified to account for the finite aperture (ie, NA) of the system, and its nominal angle of incidence. The preferred center wavelength is 550 nm, and the preferred bandwidth is 10 nm. However, there is great latitude in the choice of these parameters.

One data-processing method for the QDIC assumes that the two reflection coefficients for the sheared beams 112a and 112b are the same and do not change the polarizations of the beams. These assumptions are generally not true for grating stacks. According to the invention, the above-described method is generalized to profile over grating stacks.

Figure 18:
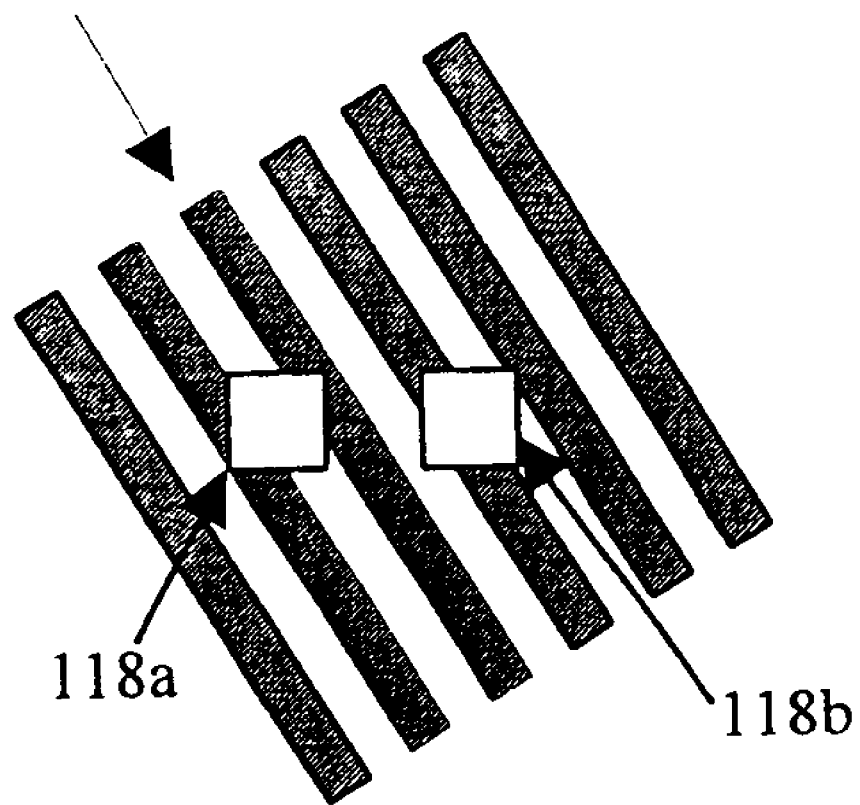
FIG. 18 illustrates a top of a misaligned array being examined by the QDIC.
Figure 19:
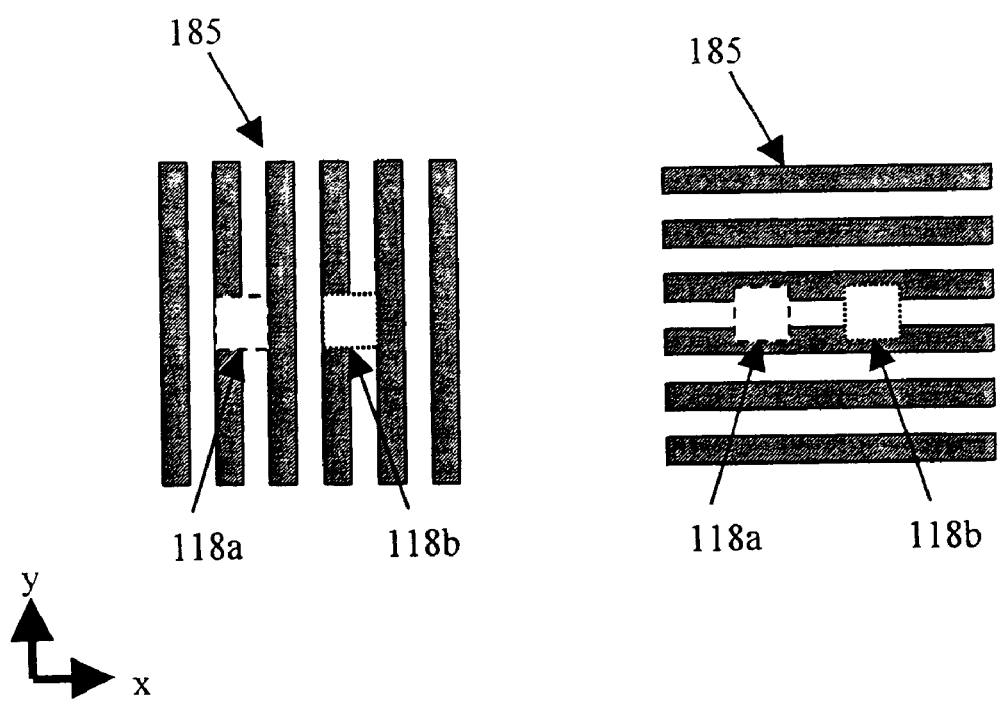
FIG. 19 illustrates the tops of aligned arrays being examined by the QDIC.

FIG. 18 shows a configuration that is not amenable to the above-described processing method. In the case illustrated in FIG. 18, the array is not aligned parallel or perpendicular to the shear direction, which is the direction of displacement between the sheared patches 118a and 118b. Thus, both patches will reflect x-polarized and y-polarized light, resulting in a QDIC giving erroneous results. FIG. 19 shows arrays 185a and 185b aligned in y and x directions, respectively, in accordance with a preferred embodiment of this invention. In a preferred embodiment, the alignment of the array maintains the polarizations of the sheared patches 118a and 118b upon reflection. The alignments of the arrays in FIG. 19 will maintain the polarizations of shear patches for the rotations of birefringent prism 80 in 90 increments discussed above.

Figure 20:
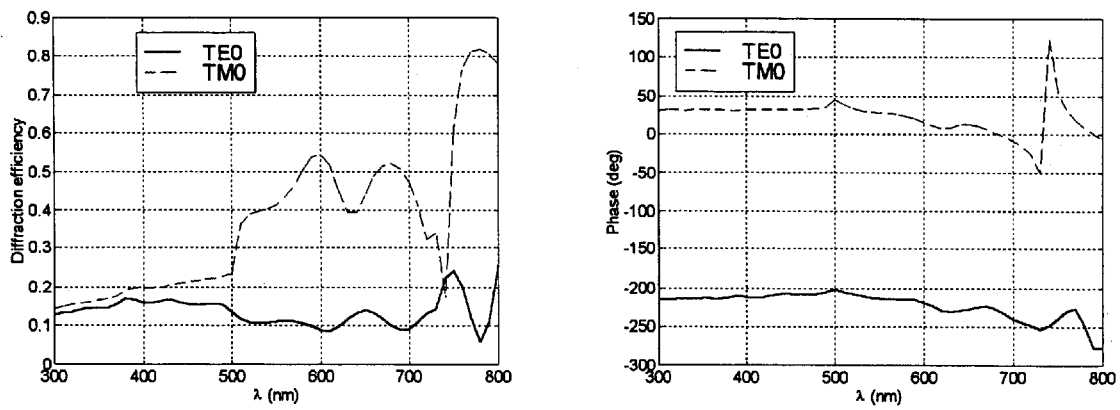
FIG. 20 shows reflection the diffraction efficiency and reflection phase for arrays aligned parallel and perpendicular to the polarization direction as functions of wavelength.

FIG. 20 shows diffraction efficiency and reflection phase for arrays aligned parallel and perpendicular to the polarization direction as functions of wavelength for normal incidence. This result was calculated by the method of Li with diffraction code Kappa (see below). The width of the copper lines and oxide spaces in the grating is 250 nm. The thickness of the grating is 1000 nm. The reflection phases are markedly different for the two polarizations. If the above-described method of Hong were applied to such a grating, it would erroneously indicate that the grating was at a slope because there would be a phase difference between the reflected sheared beams. The phase difference between the two polarizations would give hundreds of nanometers of error if not accounted for.

Figure 21:
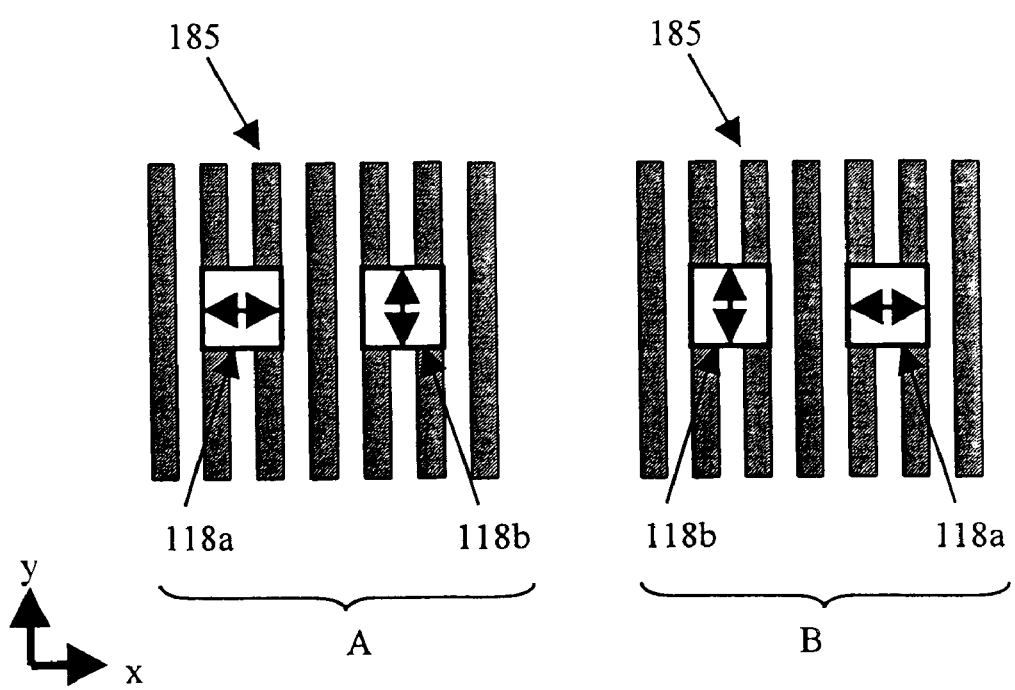
FIG. 21 shows the two configurations, A and B for symmetric operation of the QDIC.

According to the invention, then, a solution to the above-described deficiencies of the prior art techniques uses two phase images with the array direction parallel (or perpendicular) to the shear direction. The first phase difference image, collected in configuration A in FIG. 21 with birefringent prism 80 at 0°, has a form:

$$\Delta\Psi_A = (4\pi z(x+\Delta x,y)/\lambda + \Psi_{\parallel}) - (4\pi z(x-\Delta x,y)/\lambda = \Psi_{\perp})$$

$$\Delta\Psi_A = 4\pi(\Delta_x z(x,y))/\lambda + (\Psi_{\parallel} - \Psi_{\perp}) \quad (4)$$

In equation (4), z(x, y) is the height of the surface, $\Psi_{\parallel}$ is the reflection coefficient when the polarization is parallel to the grating as for shear patch 118b, $\Psi_{\perp}$ is the reflection coefficient when the polarization is perpendicular to the grating as for shear patch 118a, and $\Delta_x$ is a finite-difference operator in the x direction. The second phase difference image, collected in configuration B in FIG. 21 with birefringenent prism 80 at 180°, has the form:

$$\Delta\Psi_B = (4\pi z(x+\Delta x,y)/\lambda + \Psi_{\perp}) - (4\pi z(x-\Delta x,y)/\lambda = \Psi_{\parallel})$$

$$\Delta\Psi_B = 4\pi(\Delta_x z(x,y))/\lambda + (\Psi_{\perp} - \Psi_{\parallel}) \quad (5)$$

The average of the two images has the desired height difference without the undesired differences in reflection phase.

$$(\Delta\Psi_A + \Delta\Psi_A)/2 = 4\pi\Delta_x z(x,y)/\lambda. \quad (6)$$

The result preferably replaces the simpler form of Eq. (1) to allow profiles over grating stacks.

As described above, a homogeneous surface is defined as an area over which:

$$\Psi_r(x,y) = \Psi_{r0} \quad (7)$$

where $\Psi_{r0}$ being constant, which can be absorbed into $\Psi(0,y)$ of Eq. (1). In this case, the profile of the sample is proportional to the phase image:

$$h = \lambda \Psi(x,y)/4\lambda, \quad (8)$$

where profile h is a set of relative height profiles of the sample in x since $\Psi(0,y)$ has been neglected. This is the extent of the prior art teachings of Hong.

A heterogeneous surface is one for which $\Psi_r(x,y)$ varies in the field of view 114. In order to measure the profile h of a heterogeneous surface the ISMS preferably uses the formula $$h = \lambda[\Psi(x,y) - \Psi_r(x,y)]/4\lambda. \quad (9)$$

Thus it must have some independent information regarding $\Psi_r$ for every point on a useful profile. This is preferably provided by a combination of a priori knowledge, region identification and measurements.

The independent information required at a point depends on the stack at that point. Thus, it is necessary to create a data structure of stack information for different stacks which will be crossed by the profile and identify which points on the profile belong to which stacks. In FIG. 15, there are three stacks for which there must be a priori information: the uniform space stack which is under spots 192a, 192c, and 192e, the grating stack under spot 192b, and the simple stack under spot 192d.

For each stack, the independent information yields a full description of the stack. The optical properties of the ambient medium, and system parameters like wavelengths, numerical aperature, NA, etc. are assumed known in all cases. For a simple stack, the optical properties of the substrate are required. For a uniform stack, the number and thicknesses of layers and the properties of the layers and substrate are required. For an array stack, the number and thicknesses of layers, the properties of the layers and substrate, and array-geometry parameters are required. Measuring a stack is also referred to as characterization of the stack. Once a stack has been characterized, all of its optical properties are known, and the desired reflection coefficient $\Psi_r(x, y)$ can be calculated in the manner standard in the art, Jellison for uniform stacks and Li for arrays (below). $\Psi_r(x,y)$ is calculated for wavelength, angle of incidence and polarization employed by the interferometer.

According to the invention, the division between a priori and measured information is determined by the stack and the characterization instrument. An NIR is a preferred embodiment of the characterization instrument. An alternate embodiment comprises an SE. Other embodiments are possible, eg, any of type of variable angle ellipsometer.

For a simple stack with an NIR, the optical properties of the stack are preferably a priori knowledge. Alternatives would be the complex reflection coefficient, the reflectance and reflection phase, or any other mathematical equivalents.

For a simple stack with a SE, the optical properties of the stack are preferably a priori knowledge. Alternatives would be the complex reflection coefficient, the reflectance and reflection phase, or any other mathematical equivalents. Another alternative in this case is no a priori information or a model with unknown parameters for the optical properties, as the SE is capable of measuring the needed optical properties.

For a uniform stack with an MR, preferably the thicknesses of up to three of the layers are measured, and the rest of the additional information is known a priori. Alternatively, several thicknesses of layers and several parameters describing optical properties may be measured simultaneously. This type of characterization is done routinely with prior art devices such as a KLA/Tencor UV1050.

For a uniform stack with an SE, preferably the thicknesses of several of the layers and several parameters of their optical properties are measured, and the rest of the additional information is known a priori. Such characterization is performed routinely with the KLA/Tencor UV 1280. The SE is generally capable of characterizing more parameters in a stack, but is more difficult to implement.

For a grating stack with either an NIR or an SE, preferably the thicknesses of several of the layers and the grating profile are measured, and the rest of the additional information is known a priori. In this case, much of the a priori information is likely to be embodied in a library of instrument responses which have been precalculated for various combinations of the unknown parameters using rigorous coupled mode theory (RCMT) or an equivalent model. Here, measurement refers to minimizing the difference between calculated and measured spectra that have been pre-calculated for various combinations of the unknown parameters.

Thin-film measurement of uniform stacks with an NIR is well known in the prior art, eg, Engstrom and Hauge (see below). An INIR works the same way, except that the measurement is performed simultaneously at multiple sites. The standard method starts with a specification of the stack that has several unknown parameters to be inverted. The inverted parameters are typically thicknesses and/or parameters in models for the optical constants of the layers. In practice there is a limit to how many parameters can be inverted. Any parameters that are not inverted must be known. Typical parameters are thicknesses of some of the films. Film measurement typically has starting guesses for the inverted parameters, or ranges. It measures the parameters by fitting a theoretical reflectance (the squared magnitude of the reflection coefficient) to the measured reflectance. The values for the parameters that give the best fit and the measured values are the ending parameters. Best fit is normally defined in terms of sum over wavelengths of the squared differences between theoretical and measured reflectance. Spectra other than theoretical and measured reflectance, per se, can be used in this procedure. For example, one signal in the difference could be the raw spectrometer counts from the sample spectrometer, and the other a model for the what that spectrum should be given values for the stack's parameters.

Thin-film measurements of uniform stacks with SE (or ISE) are similiar and well known. See Jellison or Azzam (below). There are some differences. SEs typically operate at a large angle of incidence (measured from normal), typically in the range of 75°. A SE measures two numbers at every wavelength instead of one number (reflectance) for NIR. The two numbers can be expressed in many ways, but are typically expressed as the ellipsometric parameters tan $\Psi$ (not to be confused with the normal use of $\Psi$ in this document) and cos $\Delta$. Generally SE provides more information about the sample, and can be used to invert for more parameters or to achieve more precise results.

Figure 31:
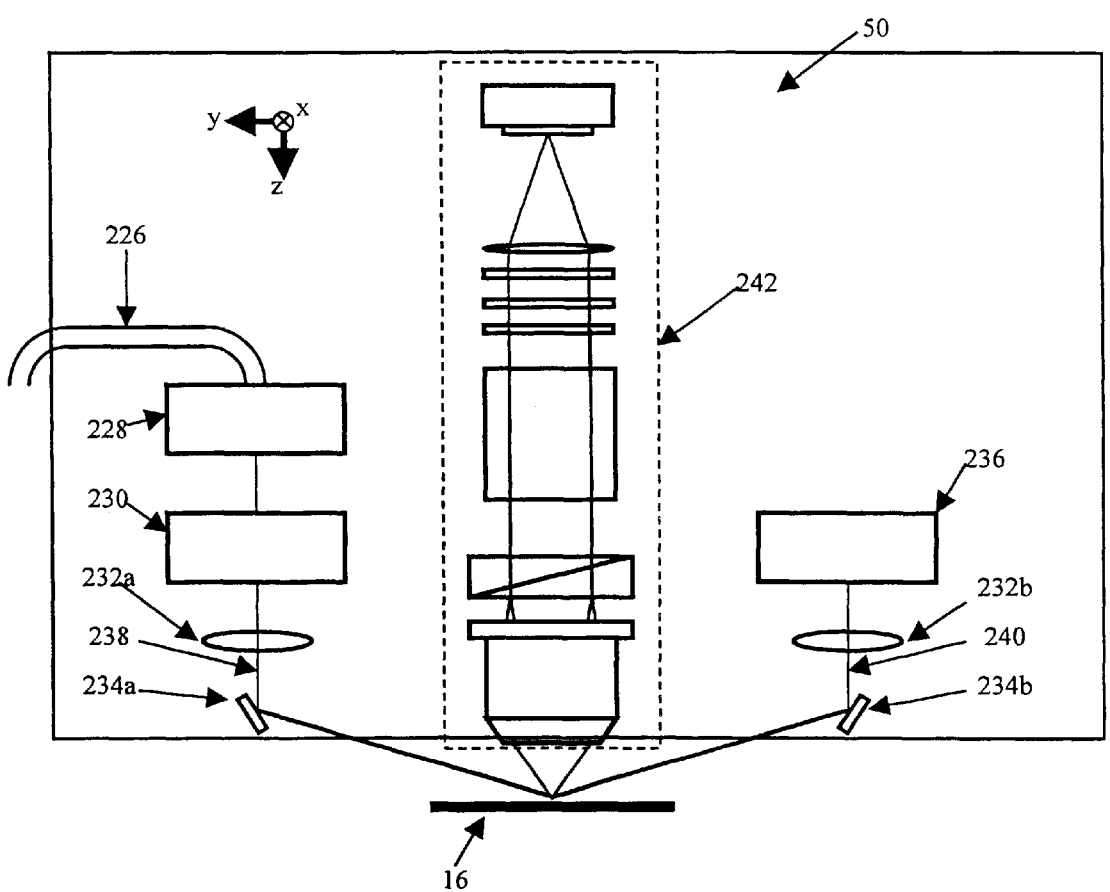
FIG. 31 is a schematic representation of an optical assembly for the ISMS incorporating a QDIC, SE and imaging system.

FIG. 31 is a schematic representation of an optical assembly for the invention comprising a QDIC, a SE, and imaging system. FIG. 31 shows an alternative embodiment of the optical assembly 50, upside down from the way it would be used in the embodiment of the ISMS shown in FIG. 4. This embodiment of the optical assembly comprises three subsystems: a quantitative differential interference contrast microscope (QDIC) as described above; an ellipsometer; and an imaging subsystem. The QDIC and imaging subsystems 242 are preferably similar to the description above, with pieces of the NIR removed. FIG. 31 shows the y-z plane, so some of the components of these previously described systems are out-of-plane, and not shown, eg, some of the illumination system. The QDIC shear direction is preferably in the x direction. The ellipsometer comprises fiber 226, illumination optics 228, polarization state generator (PSG) 230, focusing optics 232, turn mirrors 234 and polarization state detector (PSD) 236.

Fiber 226 brings light to optical assembly 50 from a white light source, preferably a xenon arc lamp. The lamp is preferably housed remotely in light box 124, as discussed above, to prevent it from heating the optical assembly. Illumination optics 228 collimate and set the aperture of the light for illumination. Preferably, illumination optics 228 yield light with a quasi-Gaussian apodization. PSG 230 creates one or more polarization states of incident light 238 to probe the sample, eg, wafer 16. Controller 126 preferably controls PSG 230. Preferably, focusing optics 232a focus the incident light 238 onto a diffraction-limited spot on the wafer. Preferably, turn mirror 234a directs incident light 238 at the wafer at the correct predetermined angle while allowing the previously described optics to be efficiently packaged. The preferred angle of incidence is in the range of 65° to 75°. Wafer 16 reflects incident light 238 as reflected light 240, and changes its state of polarization. PSD 236 detects one or more states of polarization of the reflected light. PSD 236 is preferably controlled by controller 126.

In a preferred embodiment, PSG 230 and PSD 236 each use four states of polarization so that the ellipsometer measures the full combined Mueller matrix of the optics 232, turn mirrors 234, wafer and any other intervening windows (eg, window 60). There are many other embodiments with tradeoffs between capability and simplicity, as will be appreciated by one skilled in the art. In one embodiment, PSG 230 consists largely of a rotating polarizer, and PSD 236 of a polarizer and detector. In other embodiments PSG 230 may comprise a fixed polarizer or a photo-elastic retardation modulator and polarizer. PSD 236 may comprise a rotating analyzer, or a photo-elastic retardation modulator and analyzer. In configurations where the PSD or PSG comprises primarily a stationary or rotating polarizer (analyzer), either may include a compensator.

In a preferred embodiment, light coming for fiber 226 is white light, and PSD 236 detects polarization states at multiple wavelengths. In this case, the ellipsometer is a spectroscopic ellipsometer (SE). In other embodiments the light source may be one or more lasers sequentially providing one or more wavelengths of light.

In an alternate embodiment, the ellipsometer is an imaging ellipsometer. In this case, illumination optics 228 and the focusing optics 232a focus a slit of light onto wafer 15 instead of a spot of light, and PSD 236 with the aid of focusing optics 232b detects independently reflected light from an array of points on wafer 16. For the geometry shown in FIG. 31, the array of points would be aligned on the wafer along the x direction. An additional embodiment has an imaging spectroscopic ellipsometer ISE combining the abilities of the imaging ellipsometer and the spectroscopic ellipsometer.

In other embodiments, not all of the ellipsometer components are fixed with respect to one another. In preferred embodiments the illumination optics 228, PSG 230 and PSD 236 are a first group fixed with respect to one another, and focusing optics 232 and turn mirrors 234 are a second group fixed with respect to one another. The two groups of components move in one or two dimensions with respect to one another with the addition of turn mirrors, as described for other embodiments in FIG. 10x.

Other embodiments comprise ellipsometers that operate at multiple angles, such as a scanning ellipsometer or a beam-profile ellipsometer. In a scanning ellipsometer, the angle of incidence (and detection) is controlled by mechanically scanning the components of the ellipsometer. In a beam-profile ellipsometer, the optical system separates and analyzes components of a focused beam that have propagated at different angles of incidence and reflection. An advantage of such an ellipsometer is that it is capable of doing the necessary stack characterization at the wavelength that the interferometer uses.

Figure 32:
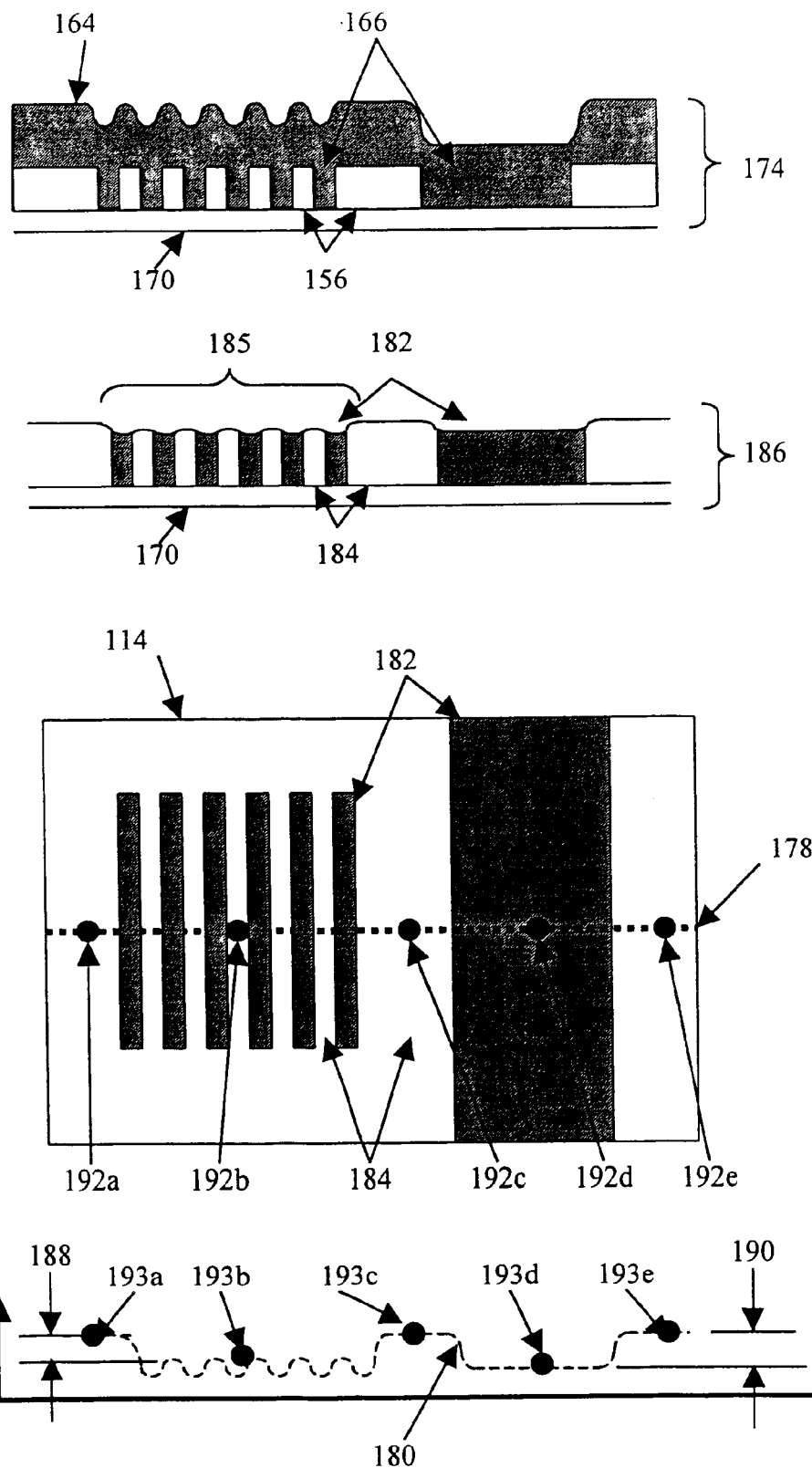
FIG. 32 illustrates an application of the preferred embodiment of the ISMS for measuring the final planarity of a damascene wafer after polishing.

FIG. 32 illustrates an application of the preferred embodiment of the ISMS for measuring the final planarity of a damascene wafer after polishing using an NIR and QDIC in combination with an imaging system. The same method would apply for data reduction if the ISMS had an SE instead of the NIR. Wafer 16 arrives at polishing machine 1 with a pre-polish damascene structure 174 with lines 166 and spaces 156 over an underlying layer 170 with as deposited copper 164. After polishing on polishing unit 14 is complete, transport system 22 moves wafer 16 to ISMS 10, which inspects wafer 16. ISMS 10 positions field-of-view 114 over the region of interest preferably using notch alignment for gross alignment, and pattern recognition applied to an image from the imaging system (with the QDIC components removed from the path) for fine alignment, with the aid of x-stage 56 and y-stages 54. One scan line 178 is chosen to characterize the planarization. In this case, the surface is heterogeneous: copper is exposed on the lines, the space stack is exposed over spaces, and array 185 is exposed. QDIC makes a phase along scan line 178. Then, the ISMS positions the NIR measurement spot sequentially at measurement points 192a–e. Profile points 193 result from use of Eqs. (8) and (9), thus incorporating measurements from the QDIC and NIR. Profile points 193a–c allow the measurement of erosion 188 and points 193c–e allow measurement of dishing 190. The dishing and erosion are reported to the polishing machine. The polishing machine 1 uses this information on sub-unit 26a to optimize the polish of subsequent wafers.

Measurement of arrays is generally more complex than measurement of uniform stacks. A method for doing so is taught by Nui for SE (below). The same method is applicable to NIR.

A database preferably contains for each stack the a priori information, a specification of what is to be measured, and starting points and or ranges for each measured parameter. The database is preferably set-up (or taught) before wafers are run. The database also contains information about where on the wafer to measure the points which make up a profile. This preferably includes pre-taught patterns to be used with a pattern recognition system at run time for the fine positioning of the array measurements, as well as gross information about where such patterns will be found on the wafer.

A preferred strategy for identifying stacks along a profile is to characterize each desired point as if it were each of the possible stacks. With each characterization, there will be a goodness-of-fit (GOF) describing the discrepancy between the measured spectrum and the theoretical spectrum based on the characterization. Identification is choosing the stack with the best goodness of fit. This method is applicable to any of the embodiments for a characterization instrument. The disadvantage of this method is that it will require a great deal of computation.

Figure 22:
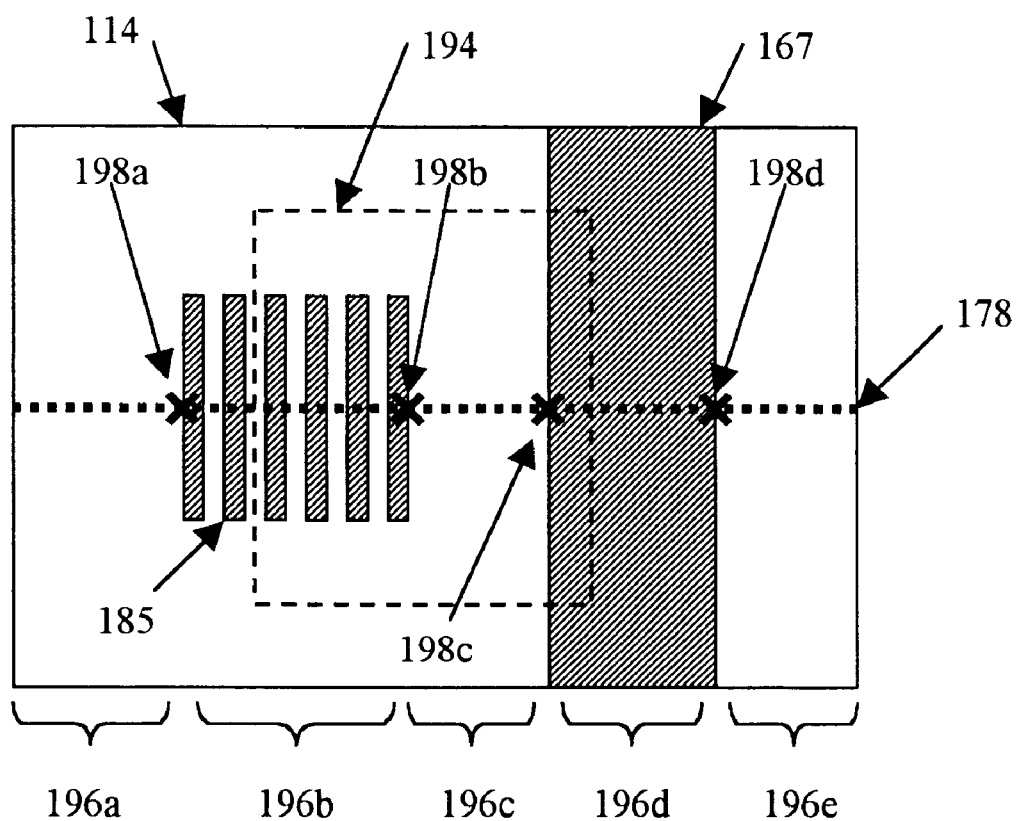
FIG. 22 illustrates boundaries and zones for stack identification at the time of training.

An alternative method for identifying stacks with stack zones is illustrated in FIG. 22. Field of view 114 contains features, in this case array 185 and wide line 167. Pattern recognition is trained in pattern-recognition domain 194. Stack boundaries 198 are defined along scan line 178 to yield stack zones 196.

At training time, the user navigates the field-of-view 114 so that it contains the features of interest. The system remembers this gross location. In this example, array 185 and wide line 198 are the features of interest. Preferably, the system with user assistance positions a pattern-recognition domain 194 over recognizable features in the image. The recognizable features are preferably the features of interest, but need not be. Then, the system identifies and remembers patterns within pattern-recognition domain 194 based on the features. This mode of operation is standard for, eg, Cognex PatMax pattern recognition software. The user identifies scan line 178 along which the profile is desired. The user further defines stack boundaries 198 that define stack zones 196 along scan line 178. The user attaches to each stack zone to a stack entry in the database. The stack entry contains whatever information is needed by the characterization instrument to yield a full characterization of the stack after characterization, as discussed above. The user also teaches the system the die pattern on the wafer.

At run time, the system identifies the location of the wafer. This is preferably done by rotating the wafer, identifying the wafer edge and notch, and rotating the wafer to a predetermined position and communicating the location of its center to the software which controls the position of optical assembly 50. The system uses this information with the trained gross position of the desired field of view to move field-of-view 114 to roughly the correct location on the wafer. At that time, pattern recognition software looks for the remembered patterns within the field of view, identifies them, and determines precisely the position of the field-of-view 114 with respect to the desired position. Preferably the system moves the field-of-view 114 precisely to the desired location on the wafer. The system collects four QDIC intensity images as described above, selects a row of pixels from each image to correspond to trained scan line 178, and produces a phase profile for that row, preferably using Eqs. (1), (2) and (6). It further processes a corresponding row of INIR pixels based on the segment 196 and information in the database. It calculates the reflection phases, subtracts them from phase profile and calculates a profile preferably using Eq. (9).

Figure 12:
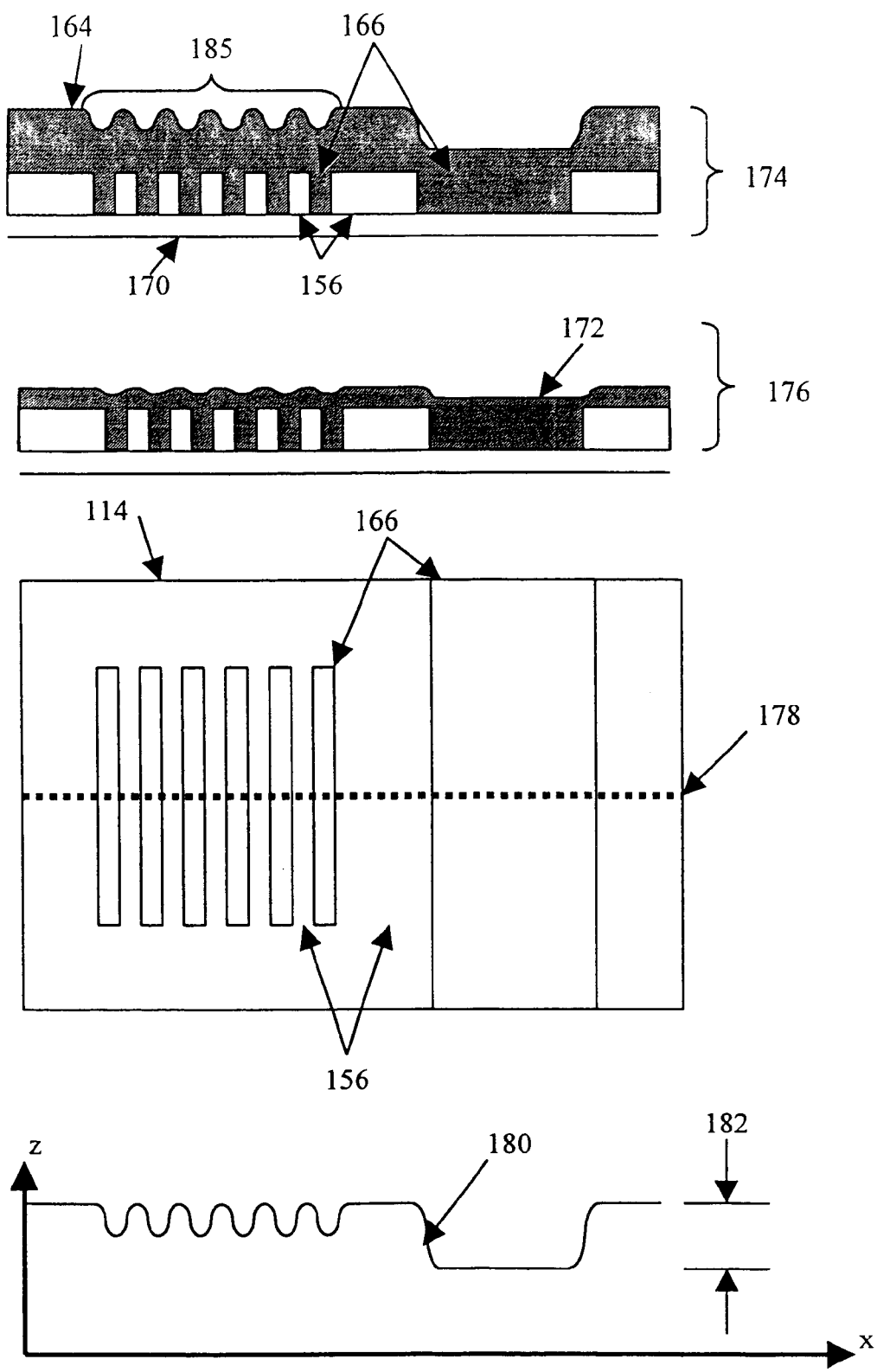
FIG. 12 illustrates one application of the ISMS for measuring the planarity of the first, selective step of a two step copper damascene process.

FIG. 12 illustrates a method employing the ISMS. In this case, a wafer 16 comes to polishing machine 1 with a pre-polish damascene structure 174 with lines 166 and spaces 156 over an underlying layer 170 with deposited copper 164. After a selective polish on polishing sub-unit 26a, the partially polished damascene structure 176 ideally has polished copper 172 covering the whole structure. At this point, transport system 22 moves wafer 16 to ISMS 10, which inspects wafer 16. ISMS 10 positions field of view 114 over the region of interest preferably using notch alignment for gross alignment, and pattern recognition applied to a DIC image (eg, $I_1$) for fine alignment, with the aid of x stage 56 and y stages 54. One scan line 178 is chosen to characterize the planarization. In this case, the surface is effectively homogeneous since copper is essentially opaque, and the profile 180 results from use of Eq. (7). From the profile the lack of planarity 182 is measured and reported to the polishing machine. The polishing machine 1 uses this information on sub-unit 26a to optimize the polish of subsequent wafers, and on sub-unit 26b to finish polishing this wafer 16a.

In the above-described method, DIC image $I_1$ is used instead of an image from the imaging system because there is no little reflectivity contrast on this wafer since it is still covered with copper. The DIC image turns profile into contrast. In an alternative embodiment, the system collects several DIC images and picks the DIC image with the most contrast. In general, if the wafer is covered with an opaque surface it is preferred to use a DIC image.

Figure 13:
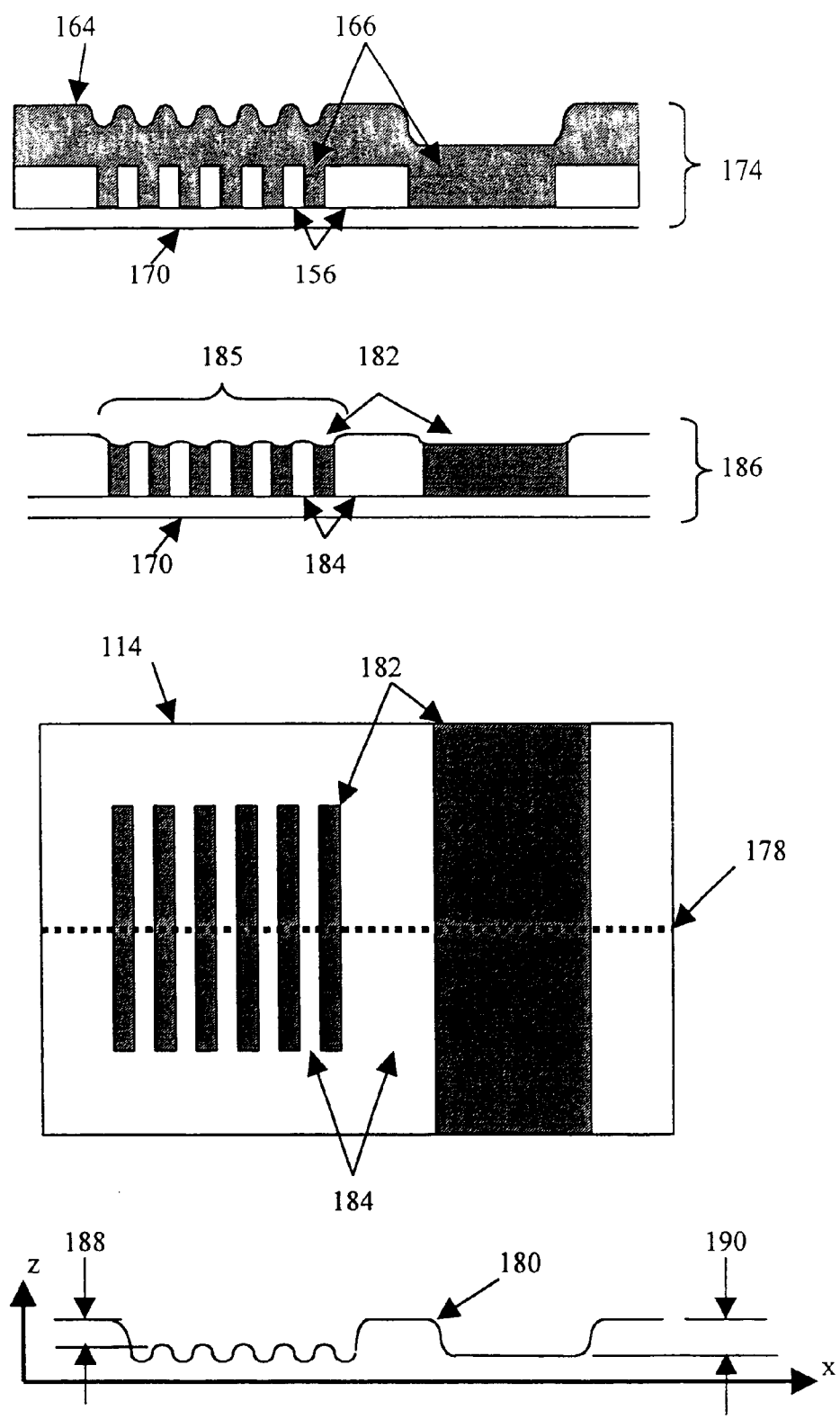
FIG. 13 illustrates on application of the ISMS for measuring the final planarity of a damascene wafer after polishing.

FIG. 13 illustrates another application of the ISMS. In this case, a wafer 16 comes to polishing machine 1 with a pre-polish damascene structure 174 with lines 166 and spaces 156 over an underlying layer 170 with as deposited copper 164. After polishing on polishing unit 14 is complete, transport system 22 moves wafer 16 to ISMS 10, which inspects wafer 16. ISMS 10 positions field-of-view 114 over the region of interest with the aid of x-stage 56 and y-stages 54; preferably using notch alignment for gross alignment and pattern recognition applied to an image from the imaging system (with the QDIC components removed from the path) for fine alignment. One scan line 178 characterizes the planarization. In this case, the surface is heterogeneous: copper is exposed on the lines, the space stack is exposed over spaces, and array 185 is exposed. The profile 180 results from use of Eqs. (8) and (9), thus incorporating measurements from the QDIC and INIR. From the profile, erosion 188 and dishing 190 are measured and reported to the polishing machine. The polishing machine uses this information on sub-unit 26a to optimize the polish of subsequent wafers.

Figure 23:
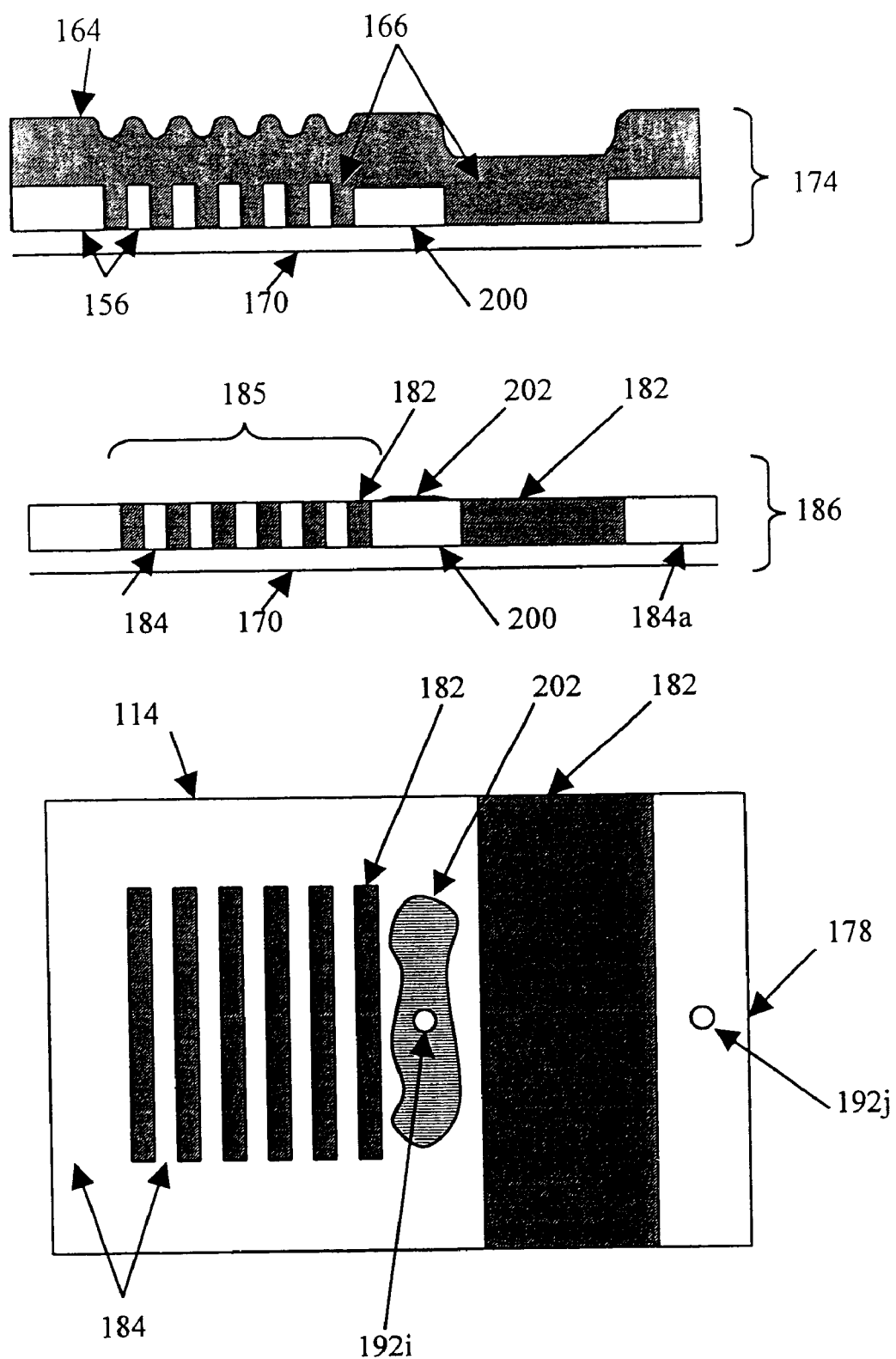
FIG. 23 illustrates an application of the ISMS for measuring copper residue on a damascene wafer after polishing.

Another method for application of the ISMS, measuring the thickness of field oxide is illustrated in FIG. 23. In this case post-polish damascene structure 186 has oxide space 184a. In the preferred method to measure the thickness of space 184a, measurement spot 192j of the NIS and field-of-view 178 are positioned over the candidate structure as shown. The stack at the measurement spot is characterized in the standard manner for a uniform stack. In the preferred embodiment NIR is used for the characterization. Preferably, constrained optimization is used to measure the thicknesses, with constraints to prevent any thickness from being negative. If INIR is used for the characterization, the method above can be followed with a single pixel or an average over a group of pixels taking the place of measurement spot 192 in FIG. 23. Alternatively and SE or an ISE can be used as the characterization instrument. In these cases, more layer thicknesses can be measured, and more characterization of material properties allowed, as is known in the art.

Another method for application of the ISMS, identification of residue is illustrated in FIG. 23. In this case, the post-polish damascene structure 186 has an oxide space 200 whose upper surface has copper residue. This may be because the top surface of space 200 is lower than that of the other oxide spaces 156, eg, to lack of planarity of the underlying stack 170, or due to deposition non-uniformity of the oxide layer that was patterned to make these spaces, or due to non-uniformity of an oxide polishing step. In other cases, the copper polishing step may have simply left residue on the top of a normal oxide space 200.

Figure 24:
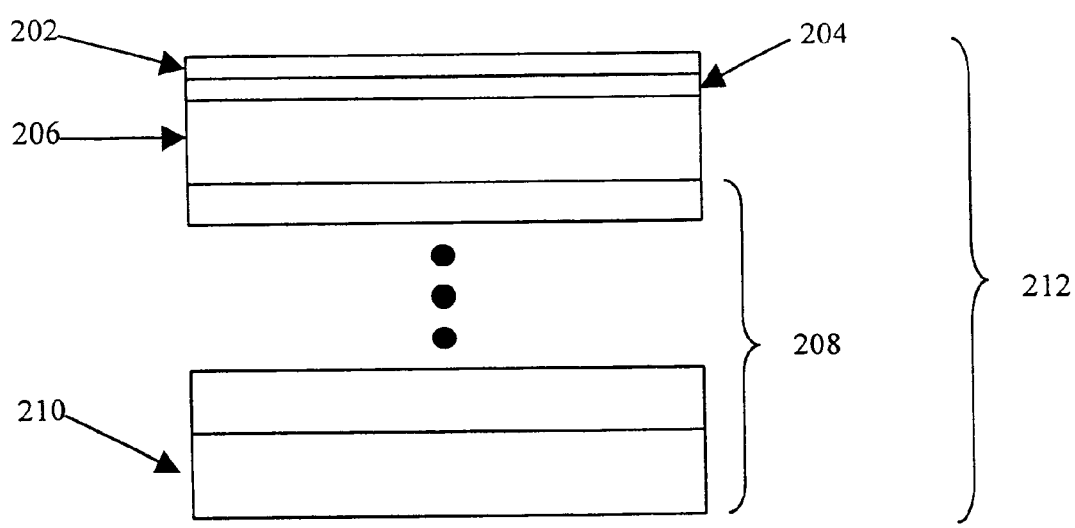
FIG. 24 illustrates a stack where residue is present.

In a preferred method to detect residue 200, measurement spot 192i of the NIS and field of view 178 are positioned over the candidate residue structure, as shown. The stack at the measurement spot is characterized in the standard manner for a uniform stack assuming the residue is present, as illustrated in FIG. 24. In a preferred embodiment, NIR is used for the characterization. A preferred stack includes residual copper 202, residual barrier 204 (eg, tantalum or tantalum nitride), top oxide 206 and underlying stack 208 including the stack substrate 210. In a preferred embodiment, the properties of all the materials and the thickness of the layers in the underlying stack 208 are known a priori, and the thicknesses of the top three layers 202, 204 and 206 are measured. Preferably, constrained optimization is used to measure the thicknesses, with constraints to prevent any thickness from being negative. Residue is detected by setting threshold on the residue layers 204 and 202. In a preferred embodiment, if either layer is measured as having a thickness greater than 0.5 nm, residue is reported, otherwise, lack of residue is reported.

There are many alternative embodiments of the method. The system can report on the presence of two or more layers of residue independently. The system can report a probability of residue taking into account the measured thicknesses and the goodness-of-fit. The system can perform a thickness measurement on a stack that does not include the residue layers, and report a poor goodness of fit as residue. This method can be refined by looking at whether the poor fit is generally due to the measured reflectivity being too high, as would be the case for a reflective layer of copper on top of a largely transparent stack. If INIR is used for the characterization, the method above can be followed with a single pixel or an average over a group of pixels taking the place of measurement spot 192i in FIG. 23. Alternatively and SE or an ISE can be used as the characterization instrument. In these cases, more layer thicknesses can be measured, and more characterization of material properties allowed, as is known in the art.

Figure 25:
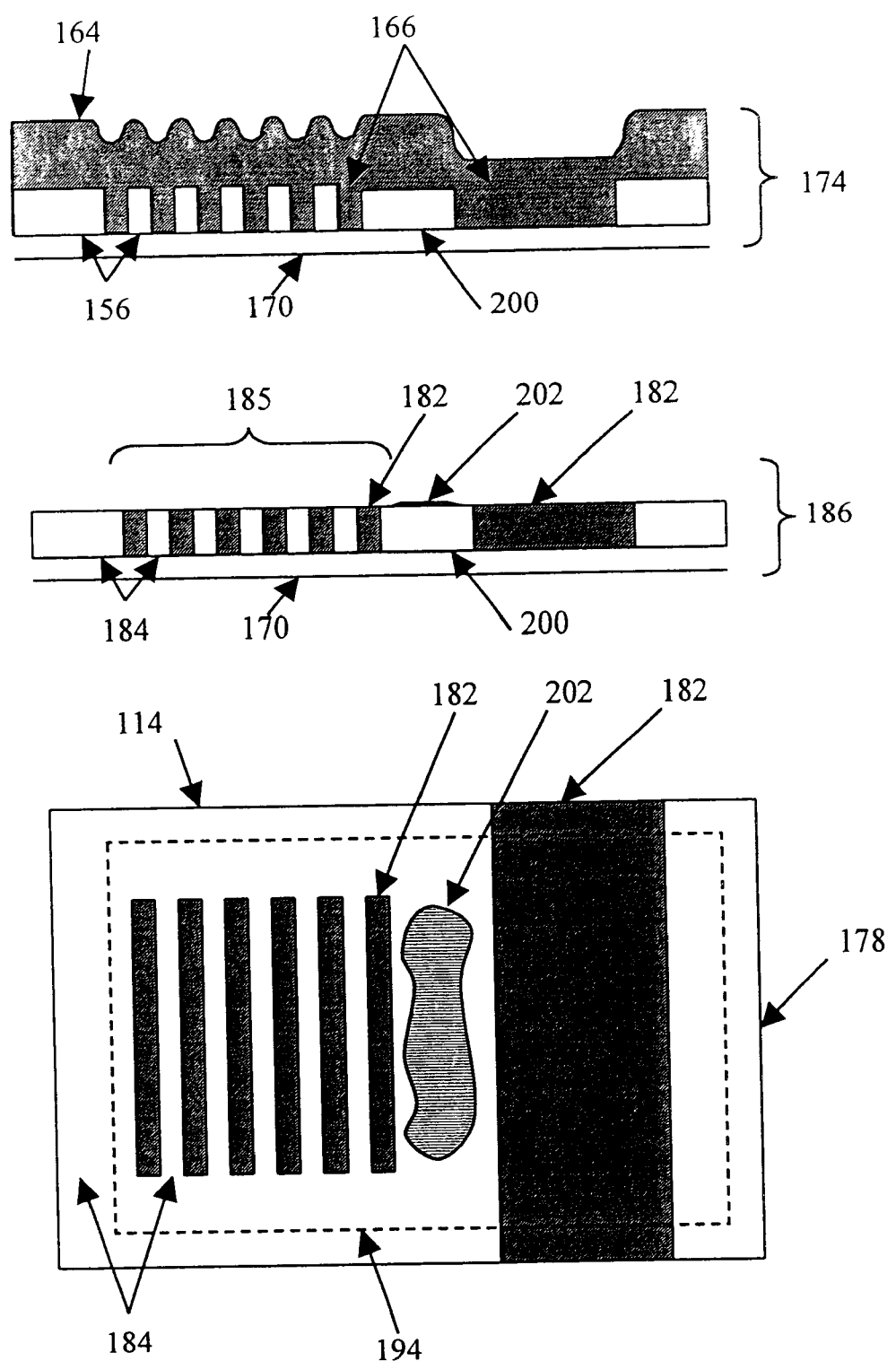
FIG. 25 illustrates application of the ISMS for locating copper residue with pattern recognition.

FIG. 25 illustrates an alternative method for detecting residue that uses pattern recognition to detect the presence of residue. In this case, the pattern recognition system is trained on a wafer that does not have residue. During training the pattern recognition system finds patterns within the pattern recognition domain 194 within field of view 178 which has been located to a region of interest on wafer 16. The patterns are due to the presence of features on the wafer, eg, lines 182 and spaces 184. At measurement time, the field of view is positioned as above, possibly using pattern recognition. The pattern recognition software examines the pattern recognition domain at run time to see if it has significant differences from the domain at training time. If there are significant differences, the system reports that there is residue. Such pattern recognition software is commercially available in the form of Cognex PatInspect.

Figure 26:
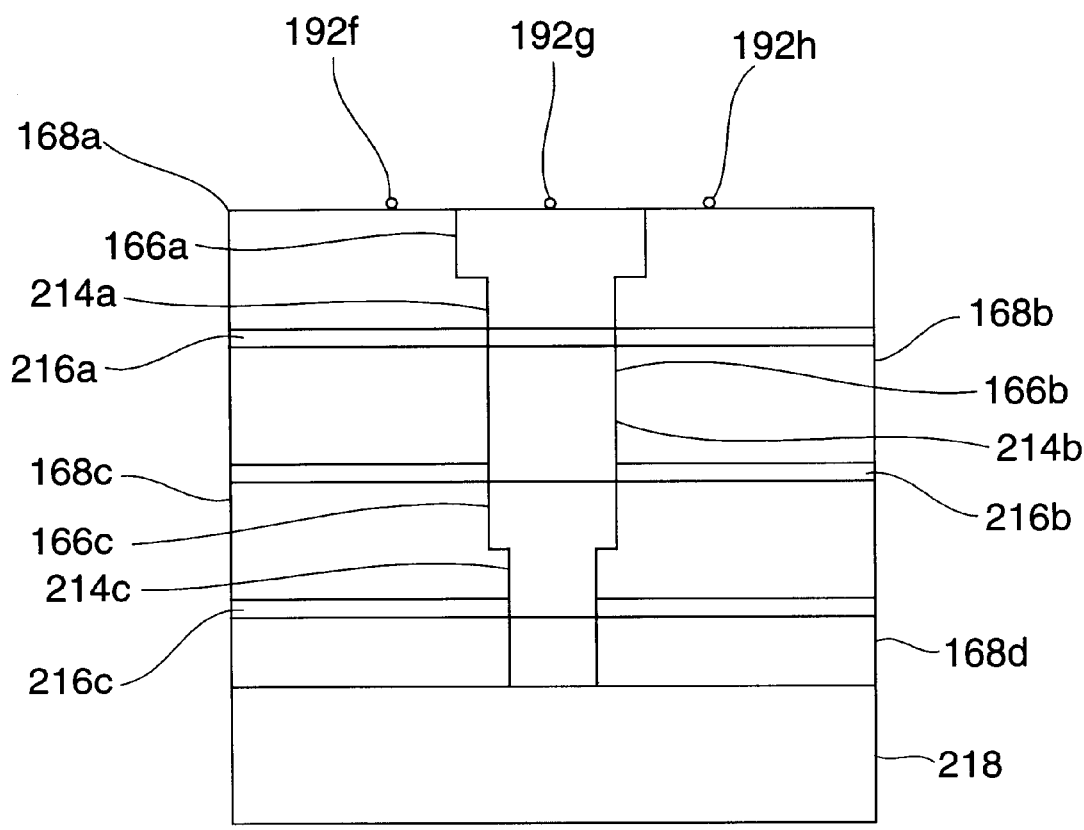
FIG. 26 illustrates prior art for the metal stack on a wafer.

FIG. 26 illustrates existing art for metal lines and plugs to interconnect an integrated circuit on a wafer. Wiring consists of multiple layers of metal lines 168 connected with plugs 214 and insulated by spaces 168. Typically, different layers of spaces are separated by a nitride etch stop 216. At the bottom level are the substrate and actual devices 218 that the metal is interconnecting. For the current application, line 166a might have just been polished and is to be examined for dishing. Dishing is defined as the difference in the height along the top surface between a high level in the neighboring oxide 168a and a low level in the metal line 166a. Thus the oxide at measurement spots 192f and 192h would be compared to the metal level at spot 192g. The problem is that the effective stack at points 192f and 192h are very thick and rather complex in that there are many transparent layers. In this case the results may be erratic because the interference fringes in the stack reflectivity are so close together. Or the lack of planarity of lower layers, eg 168b, may alias as lack of planarity in the current layer. This illustration of the problem uses dishing of a wide line as the example. The same problem exists for measuring erosion of an array in an upper layer of the metal structure.

Figure 27:
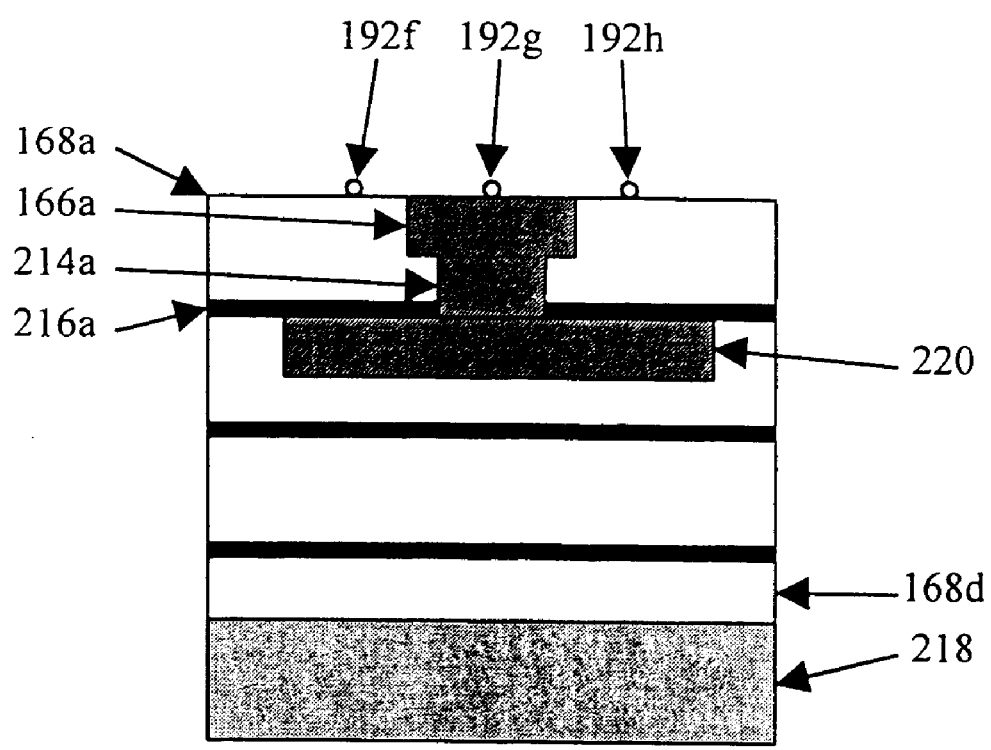
FIG. 27 illustrates a novel test structure for dishing measurements with an method of the invention.

FIG. 27 shows an aspect of the current invention addressing the above-identified problem. A dummy reflector 220 of metal has been put below line 166a and the neighboring portion of space 168a. The dummy reflector becomes the stack substrate at spots 192f and 192h, so that the methods described above can be used to measure the erosion of line 192g. In some embodiments the dummy reflector 220 can be placed below a live line, ie, one that is used to connect circuits. This would be possible if that volume is not used for other live interconnects. In a preferred embodiment of the invention, line 192g and the surrounding oxide are dedicated for metrology purposes as a test structure, and do not serve any purpose for interconnection. While test structures for transparent materials are used in the current art of film thickness metrology, test structures for measuring planarity of a surface are not.

Figure 28:
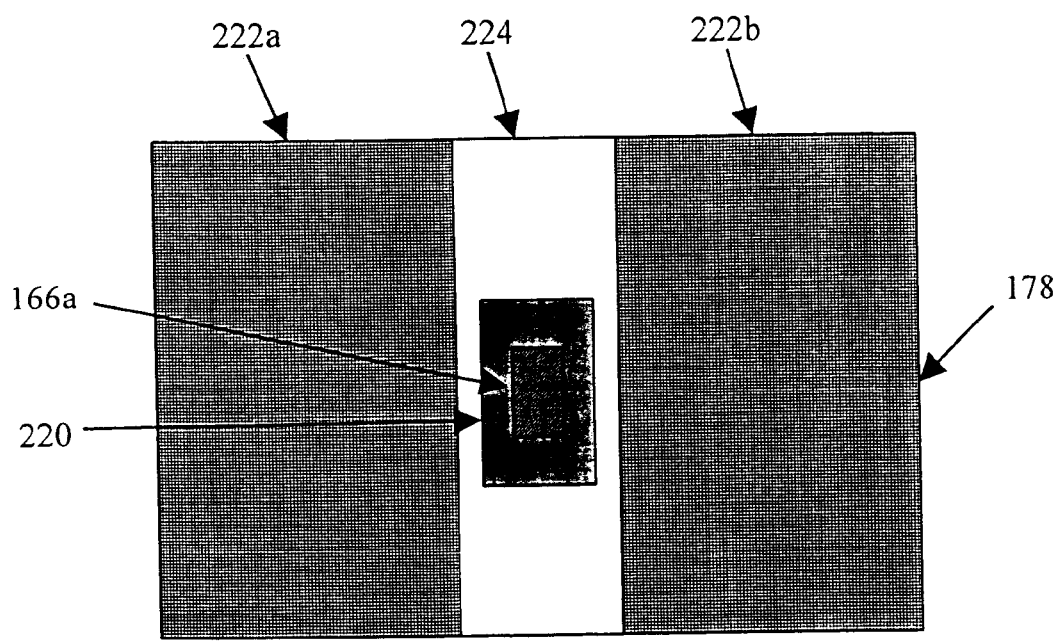
FIG. 28 illustrates the placement of a dishing test structure in the scribe line of a wafer.

FIG. 28 shows the preferred embodiment for a test structure. The structure consists of line 166a, dummy reflector 220, and the oxide above dummy reflector 220. The structure is positioned in scribed line 224 between device dies 222a and 222b on the wafer. In this way, the test structure does not interfere with the operation of the electrical circuits in the die, and uses space that cannot be used for circuitry, as the wafer will be cut along the scribe line to make individual integrated circuits.

Figure 29:
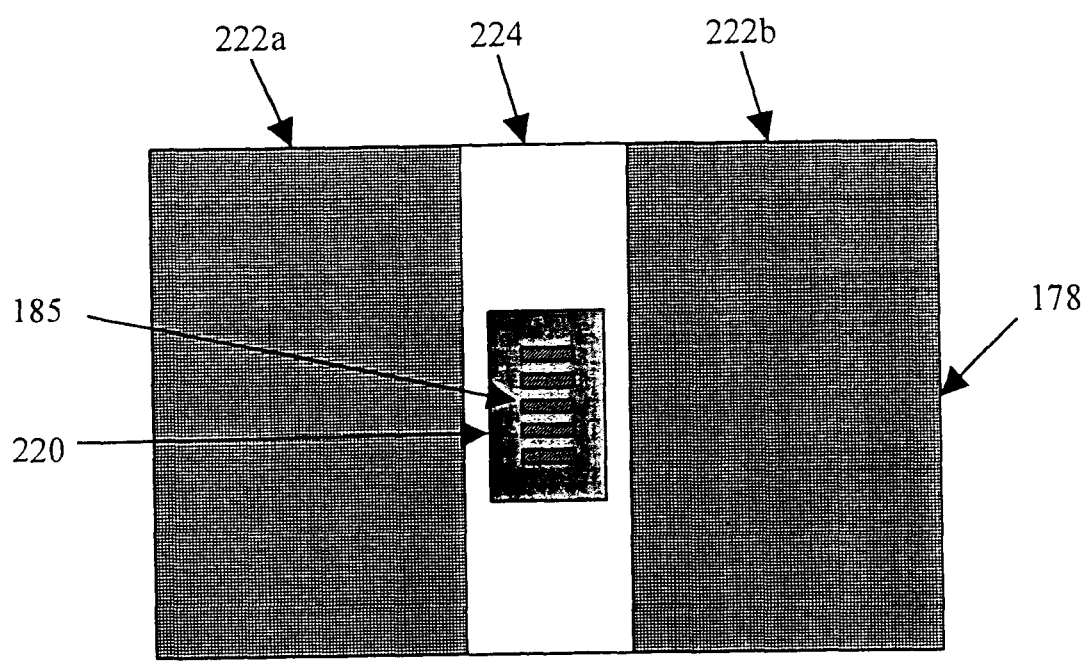
FIG. 29 illustrates the placement of a erosion test structure in the scribe line of a wafer.

Another preferred embodiment is shown in FIG. 29. In FIG. 29, the test structure consists of array 185 on a top surface of the wafer, the surrounding oxide, and dummy reflector 220 on a layer below the top layer. The purpose of this test structure is to measure erosion. In other embodiments of test structures, they are placed somewhere within the die, so that measurements on the test structure will be more representative of the device region of the wafer.

Another method for using the ISMS with a QDIC, to create a two-dimensional profile of the sample, is illustrated in FIG. 25. The QDIC produces a first set of x phase profiles 260 with birefringent prism 80 at 0°, and a second set of y phase profiles 262 with birefringent prism 80 at 90°. The preferred camera 98 is 640 pixels wide in x, and 480 pixels high in y. Thus there are 1120 one dimensional profiles. The x profiles in x set 260 are disconnected due to the unknown $\Psi(0, y)$ in Eq. (2). There is one unknown number for each profile, ie, 480 unknowns for the x profiles. Similarly the y profiles in set 262 have 640 unknown numbers $\Psi(x,0)$ associated with them. Controller 126 then processes these two sets of one dimensional profiles to yield the two-dimensional, x-y profile 264 by solving for the 1120=480+ 640 unknowns. This is preferably treated as a least squares problem which minimizes the sum of the squares of two corrected sets of profiles. A corrected profile is one where the unknown parameters for that profile, $\Psi(0,y)$ or $\Psi(x,0)$ have been set. The optimized profiles are the two profiles that minimize the sum of the squares of their pixel-by-pixel differences. The two-dimensional profile is the mean of the two optimized profiles. There are many alternative embodiments for processing the two sets of profiles to yield a two-dimensional profile.

According to the invention, the ISMS comprises various sub-systems and represents an integrated optical measurement approach for nanometer-scale measurement, modeling and data analysis with a rugged, compact and high throughput design. It can be readily appreciated that these features can be applied to a wide variety of industrial situations, wherever there is a need to measure surface characteristics and topography for process control.

For example, lithography is increasingly becoming the key driver for shrinking the feature size to 150 nm and beyond in semiconductor fabrication. The continued growth of the industry relies on significant advancements in metrology and process control. A variety of factors in the processing scheme can all contribute to the total variation in the CD (critical dimension) of features, while the CD budget is extremely tight. However, the predominant method of process control in lithography is based on off-line measurement.

As the disk-drive industry pushes itself to meet the future demands for increased storage capacity, there is greater need for process control in the manufacture of disks and magnetic heads. Important measurable quantities for disks include planarity of disk blanks before and after polishing and coating and the topography of symmetrical "donut-shaped" laser textured bumps including the bump feature size.

For magnetic heads, the flatness of the air-bearing surfaces is critical. Other applications in hard disk and magnetic media include: i) microwaviness and three dimensional characterization; ii) Duboff analysis: measuring to chamfer at the edge of a disk; iii) Reflective disk flatness (RVA); iv) Transparent disk flatness; v) slider taper testing-process control and development; vi.) TPC thin-film step height; vii) Automatic ABS shape measurement. (Source: ADE/Phase Shift).

The invention finds general utility in a broad field of precision manufacturing. An integrated metrology tool according to this invention or in-line (self-contained, industrially hardened, factory floor) embodiments are adaptable to providing back to grinding, honing, polishing, lapping and super-finishing processes, thereby permitting these machines to produce more reliable and consistent parts. Several exemplary applications are immediately apparent: 1) Ground and polished valve seat; 2) Sealing surface of fuel injectors; 3) Engine valve stems; 4) High precision bearings; 5) high-polish ceramic parts. Other applications include tightly-controlled coating and electroplating processes such as lead frames, high performance polymer surfaces, and coated paper roughness.

Embodiments of the invention are also adaptable to optics and medical device manufacturing. Almost all of precision optics such as lenses, mirrors, prisms and windows require precise measurement of surface figures-of-merit. Embodiments of the invention are also adaptable to medical device manufacture includeing: 1) Contact lens manufacturing; 2) Roughness control of metal stents; and 3) Surface characteristics of prosthetic joints.

The Following Documents are Incorporated in Their Entirety by Reference

[5] C. M. Peyne et al., 'Test structures for characterizing a Damascene CMP interconnect process', Proc. EEE 1997 Int. conference on Microelectronic Test Structures, Vol 10, March 1997. 151–155.

[6] C. J. Morath et al., 'Ultrasonic multilayer metal film metrology', Solid State Technology, June 1997, 85–92.

[7] Michael A. Joffe et al, 'Novel thin-film metrology for CMP applications', 1999 Proceedings of the Fourth International Chemical-Mechanical Planarization for ULSI Multilevel Interconnection Conference (CMP-MIC), 73–76.

[8] Gao Hong, Xin Qiming, and Robert E. Parks, "Three-dimensional optical profiler using nomarski interferometery", SPIE Proceedings Vol. 1994, Fabrication and Testing of Optics and Large Optics, 1994, Meeting Date: Jul 11–Jul. 16, 1993, San Diego, Calif., USA, 150–153.

[9] Timothy R. Corle and Gordon S. Kino, 'Differential interference contrast imaging on a real time confocal scanning optical microscope', Applied Optics, Vol. 29, No. 26 (1990) 3769–3774.

[10] Delbert L. Lessor et al, 'Quantitative surface topography determination by Nomarski reflection microscopy. I. Theory', J.Opt.Soc.Am. Vol. 69, No. 2 (1979) 357–366.

[11] John S. Hartman et al., "Quantitative surface topography determination by Nomarski reflection microscopy. 2: Microscope modification, calibration, and planar sample experiments", Applied Optics, Vol. 19, No. 17 (1980) 2998–3009.

[12] See for example http://www.chapinst.com/how it works.htm. Chapman Instruments profilers use the Nomarski method in a scanning rather than imaging configuration.

[13] U.S. Pat. No. 5,436,725 "Confocal Optical System for Thickness Measurements of Patterned Wafers".

[14] xinhui Niu et al., 'Specular Spectroscopic Scatterometry in DUV Lithography', SPIE 24$^{th}$ International Symposium on Microlithography, SPEE Paper 3677–18 (1999).

[15] Duane Boning et al., 'MIT/Sematech 931 AZ Cu CMP Characterization Test Chip', Sematech Technology Transfer #98103580A-TR (1998).

[16] Stephan A. Coulombe et al, 'Ellipsometric Scatterometry for sub-0.1 micron CD measurements', SPIE Vol. 3332 (1998) 282–293.

[17] Jörg Bischoff et al., 'Optical Scatterometry of quarter micron patterns using neural regression', SPIE Vol. 3332 (1998) 526–537.

[18] Björn Karlsson, 'Detector and Data Acquisition System for an Imaging Ellipsometer', IEEE Instrumentation and Measurement Technology Conference, St. Paul Minn. (1998) 679–682.

[19] T. Ganz et al., 'Microellipsometry', see http://gaston.iap.physik.tu-darmstadt.de/omt/ib97 mic.ps.

[20] Holger Jennewein et al, 'Interferometrical Profilometry at Surfaces with Varying materials', SPIE 24$^{th}$ International Symposium on Microlithography, SPIE Paper 3677–109 (1999).

[21] G. Springer, 'Dependence of water carrier motor current and polish pad surface temperature signal on CMP consumable conditions and Ti/TiN liner deposition parameters for Tungsten CMP endpoint detection', 1999 Proceedings of the Fourth International Chemical-Mechanical Planarization for ULSI Multilevel Interconnection Conference (CMP-MIC), 45–51.

[22] Lifeng Li, 'Multilayer modal method for diffraction gratings of arbitrary profile, depth and permittivity', Jour. Opt. Soc. of Am. A/Vol. 10, No 12 (1993) 2581–2591.

[23] *The Handbook of Optics*, Vol II, Michael Bass, ed., McGraw Hill, Inc, New York (1995).

[24] Hauge, P. S., "Polycrystalline silicon film thickness measurement from analysis of visible reflectance spectra", J. Opt. Soc. Am, 69 No. 8, August 1979.

[25] Engstrom, Herbert, "Measuring thickness of a film deposited onto a multilayer metal surface", SPIE Vol. 173 Integrated Circuit Metrology, Inspection, and Process Control VI (1992).

[25] Jellsion, G. E. Jr., "Data Analysis for spectroscopic ellipsometry", Thin Solid Films, 234 (1993) 416–422.

[26] Azzam, Rasheed M. A., "Ellipsometry", Chapter 27 in *The Handbook of Optics*, Vol II, Michael Bass, ed., McGraw Hill, Inc, New York (1995).

U.S. Pat. No. 5,517,312 Jun. 5, 1996 Finarov.
U.S. Pat. No. 5,764,365 Jun. 6, 1998 Finarov.

What is claimed is:

1. A wafer polishing system with the integrated capability to measure wafers after polishing, said wafers having structure formed on the surface comprised of one or more stacks, said system comprising:

a polisher station;

an optical profilometer for evaluating variations in height of the wafer by measuring the relative optical phase of a light beam reflected off of measurement points on the wafer;

an optical characterization monitor selected from a group consisting of a spectroscopic reflectometer and a spectroscopic ellipsometer, said characterization monitor providing information about the dimensions and/or optical characteristics of the structure such that the effect of the dimensions and optical characteristics of the structure on the measured phase of the light beam in the optical profilometer can be considered in determining the variations of the height of the wafer surface; and a wafer handler for transferring wafers between the polisher station and the optical profilometer and the optical characterization monitor.

2. A polishing system as recited in claim 1, wherein said optical profilometer is selected from the group consisting of a differential interference contrast, quantitative differential interference contrast, white-light point-diffraction interferometry, phase-shift interferometry, heterodyne interferometry and phase retrieval from transport-of-intensity systems.

3. A polishing system as recited in claim 1, wherein said optical characterization monitor includes a polychromatic light beam which is directed onto the wafer with an optical element and wherein the probe beam of the optical profilometer is directed onto the wafer with the same optical element.

4. A polishing system as recited in claim 1, wherein said optical characterization monitor further functions to determine the diffraction characteristics of the structure.

5. A polishing system as recited in claim 1, wherein said optical characterization monitor is a normal incidence spectroscopic reflectometer.

6. A polishing system as recited in claim 5, wherein said optical profilometer is a common path differential interference contrast interferometer.

7. A polishing system as recited in claim 1, wherein said optical characterization monitor measures at single points.

8. A polishing system as recited in claim 1, wherein said optical characterization monitor is an imaging instrument.

9. A method of determining the optical profile of a wafer having a structure formed on the surface comprised of one or more stacks, said method comprising the steps of:

evaluating changes in the height of the wafer using an optical profilometer which measures the relative optical phase of light reflected from measurement points on the wafer; and determining the optical characteristics and/or dimensions of the structure on the wafer using one of a spectroscopic reflectometer and a spectroscopic ellipsometer, wherein the effects of the optical characteristics and dimensions of the stack on the measured phase of the reflected light in the optical profilometer can be considered in determining the variations in the height of the wafer surface.

* * * * *